(12) United States Patent
Negiz et al.

(10) Patent No.: US 9,174,892 B2
(45) Date of Patent: Nov. 3, 2015

(54) PROCESS FOR INCREASING A MOLE RATIO OF METHYL TO PHENYL

(71) Applicant: UOP LLC, Des Plaines, IL (US)

(72) Inventors: Antoine Negiz, Wilmette, IL (US); Edwin P. Boldingh, Arlington Heights, IL (US); Gregory J. Gajda, Mount Prospect, IL (US); Dean E. Rende, Arlington Heights, IL (US); James E. Rekoske, Glenview, IL (US); David E. Mackowiak, Mount Prospect, IL (US); Paul T. Barger, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/066,982

(22) Filed: Oct. 30, 2013

(65) Prior Publication Data
US 2014/0058157 A1 Feb. 27, 2014

Related U.S. Application Data

(63) Continuation-in-part of application No. 12/689,560, filed on Jan. 19, 2010, now Pat. No. 8,598,395.

(51) Int. Cl.
| | |
|---|---|
| *C07C 2/66* | (2006.01) |
| *C10G 29/20* | (2006.01) |
| *C10G 35/06* | (2006.01) |
| *B01J 29/18* | (2006.01) |
| *B01J 29/40* | (2006.01) |
| *B01J 29/70* | (2006.01) |

(52) U.S. Cl.
CPC ............... *C07C 2/66* (2013.01); *C10G 29/205* (2013.01); *C10G 35/065* (2013.01); *B01J 29/18* (2013.01); *B01J 29/40* (2013.01); *B01J 29/7034* (2013.01); *B01J 2229/42* (2013.01); *C10G 2300/104* (2013.01); *C10G 2300/1044* (2013.01); *C10G 2300/1081* (2013.01); *C10G 2300/1096* (2013.01); *C10G 2400/02* (2013.01); *C10G 2400/30* (2013.01)

(58) Field of Classification Search
USPC .......................................... 585/467
See application file for complete search history.

(56) References Cited

U.S. PATENT DOCUMENTS

| 2,168,590 A | * | 8/1939 | Taylor ........................... 585/470 |
| 5,434,326 A | * | 7/1995 | Gajda et al. .................. 585/467 |

FOREIGN PATENT DOCUMENTS

| EP | 0250879 A1 | 1/1988 |
| EP | 0528088 A1 | 2/1993 |
| JP | 638343 | 1/1988 |
| JP | 5057193 | 3/1993 |
| JP | 2005529978 | 10/2005 |
| JP | 2009545548 | 12/2009 |
| WO | 95/05433 A1 | 2/1995 |
| WO | 2004000974 | 12/2003 |
| WO | 2008015027 A1 | 2/2008 |

OTHER PUBLICATIONS

Extended European Search Report dated May 8, 2015 for Application No./Patent No. 11735009.0-1454/2526164 PCT/US2011021079.

* cited by examiner

*Primary Examiner* — Thuan D Dang

(57) ABSTRACT

One exemplary embodiment can be a process for increasing a mole ratio of methyl to phenyl of one or more aromatic compounds in a feed. The process can include reacting an effective amount of one or more aromatic compounds and an effective amount of one or more aromatic methylating agents to form a product having a mole ratio of methyl to phenyl of at least about 0.1:1 greater than the feed.

6 Claims, 24 Drawing Sheets

Comparison of toluene yield as a function of bed temperature between nickel Catalyst A and non-metal zeolite Catalysts B, C, and D.

Comparison of xylene yield as a function of bed temperature between nickel Catalyst A and non-metal zeolite Catalysts B, C, and D.

Comparison of ethylbenzene yield as a function of bed temperature between nickel Catalyst A and non-metal zeolite Catalysts B, C, and D.

Comparison of aromatic ring recovery as a function of bed temperature between nickel Catalyst A and non-metal zeolite Catalysts B, C, and D.

Comparison of the methyl to phenyl ratio as a function of benzene conversion between nickel Catalyst A and non-metal zeolite Catalysts B, C, and D.

Comparison of toluene yield as a function of bed temperature between non-metal catalysts B, C, D, and E.

Comparison of xylene yield as a function of bed temperature between non-metal catalysts B, C, D, and E.

Comparison of ethylbenzene yield as a function of bed temperature between non-metal catalysts B, C, D, and E.

Comparison of aromatic ring recover as a function of bed temperature between non-metal catalysts B, C, D, and E.

Comparison of methyl to phenyl ratio as a function of benzene conversion between non-metal catalysts B, C, D, and E.

Comparison of toluene yield versus bed temperature between metal containing and non-metal containing MFI and MTW zeolite catalysts.

Comparison of xylene yield versus bed temperature between metal containing and non-metal containing MFI and MTW zeolite catalysts.

Comparison of ethylbenzene yield versus bed temperature between metal containing and non-metal containing MFI and MTW zeolite catalysts.

Comparison of aromatic ring recovery versus bed temperature between metal containing and non-metal containing MFI and MTW zeolite catalysts.

Comparison of methyl to phenyl ratio versus benzene conversion between metal containing and non-metal containing MFI and MTW zeolite catalysts.

Comparison of toluene yield as a function of bed temperature between non-metal, platinum containing, and rhenium containing MFI zeolite catalysts.

Comparison of xylene yield as a function of bed temperature between non-metal, platinum containing, and rhenium containing MFI zeolite catalysts.

Comparison of ethylbenzene yield as a function of bed temperature between non-metal, platinum containing, and rhenium containing MFI zeolite catalysts.

Comparison of aromatic ring recovery as a function of bed temperature between non-metal, platinum containing, and rhenium containing MFI zeolite catalysts.

Comparison of methyl to phenyl ratio as a function of benzene conversion between non-metal, platinum containing, and rhenium containing MFI zeolite catalysts.

Comparison of toluene yield as a function of bed temperature between rhenium and non-rhenium containing UZM-8 and MFI zeolite catalysts.

Comparison of xylene yield as a function of bed temperature between rhenium and non-rhenium containing UZM-8 and MFI zeolite catalysts.

Comparison of ethylbenzene yield as a function of bed temperature between rhenium and non-rhenium containing UZM-8 and MFI zeolite catalysts.

Comparison of aromatic ring recovery as a function of bed temperature between rhenium and non-rhenium containing UZM-8 and MFI zeolite catalysts.

Comparison of methyl to phenyl ratio as a function of benzene conversion between rhenium and non-rhenium containing UZM-8 and MFI zeolite catalysts.

Comparison of toluene yield as a function of bed temperature between Catalysts K, L, M, N, O.

% Xylene Yield at the Conditions of FIG. 26.

Comparison of Xylene yield as a function of bed temperature between Catalysts F, K, P, Q, R.

Comparison of Toluene yield as a function of bed temperature between Catalysts F, K, P, Q, R.

Comparison of Xylene yield as a function of bed temperature between Catalysts S and M plus Catalysts T and N.

Comparison of Toluene yield as a function of bed temperature between Catalysts S and M plus Catalysts T and N.

Comparison of Xylene yield as a function of bed temperature between Catalysts U and V.

Comparison of Toluene yield as a function of bed temperature between Catalysts U and V.

Comparison of Xylene yield versus Benzene Conversion between Catalysts W and X.

Comparison of EthylBenzene yield as a function of bed temperature between Catalysts W and X.

Comparison of Toluene yield as a function of bed temperature between Catalysts W and X.

Comparison of Methane yield as a function of bed temperature between Catalysts W and X.

Comparison of Toluene yield as a function of bed temperature between Catalysts Y, Q and A.

Comparison of Xylene yield as a function of bed temperature between Catalysts Y, Q and A.

Comparison of Toluene yield as a function of bed temperature between Catalysts L, M, U, and Y.

Comparison of Xylene yield as a function of bed temperature between Catalysts L, M, U, and Y.

Comparison of Toluene yield as a function of bed temperature between Catalysts Y, Z, and AA.

Comparison of Xylene yield as a function of bed temperature between Catalysts Y, Z, and AA.

Comparison of Toluene yield as a function of bed temperature between Catalysts U, AB, and AC.

Comparison of Xylene yield as a function of bed temperature between Catalysts U, AB, and AC.

Comparison of Toluene yield as a function of bed temperature between Catalysts M, AD, and AE.

Comparison of Xylene yield as a function of bed temperature between Catalysts M, AD, and AE.

PROCESS FOR INCREASING A MOLE RATIO OF METHYL TO PHENYL

CROSS REFERENCE TO RELATED APPLICATION

This application is a Continuation-in-Part of prior copending application Ser. No. 12/689,560 which was filed on Jan. 19, 2010, the contents of which are incorporated herein by reference thereto.

FIELD OF THE INVENTION

This invention generally relates to a process for increasing a mole ratio of methyl to phenyl of, e.g., one or more aromatic compounds.

DESCRIPTION OF THE RELATED ART

Typically, an aromatic complex can process a hydrotreated naphtha feed to produce various products, such as benzene and one or more xylenes. However, it may be desirable to produce higher substituted aromatics, depending, e.g., on market conditions. In addition, when producing motor fuel products, increasingly stringent environmental regulations can require lower benzene content. As a consequence, there is a demand for alternative processes for removing benzene from, e.g., gasoline. Thus, systems and processes that allow flexibility to convert benzene to other and higher valued products may be desirable.

However, existing processes can use expensive catalysts and/or reactants that can require further processing to separate undesirable side products. Thus, it would be advantageous to provide an agent that can convert benzene to other substituted aromatics while minimizing undesirable products and/or side reactions.

SUMMARY OF THE INVENTION

One exemplary embodiment can be a process for increasing a mole ratio of methyl to phenyl of one or more aromatic compounds in a feed. The process can include reacting an effective amount of one or more aromatic compounds and an effective amount of one or more aromatic methylating agents to form a product having a mole ratio of methyl to phenyl of at least about 0.1:1 greater than the feed.

Another exemplary embodiment may be a process for reacting one or more aromatic compounds in a feed. The process may include reacting the feed including an effective amount of one or more aromatic compounds and an effective amount of one or more aromatic methylating agents to obtain a product having an aromatic ring recovery of about 85-about 115%, by mole, with respect to the feed and having a mole ratio of methyl to phenyl of at least about 0.1:1 greater than the feed.

Yet another exemplary embodiment can be a process for increasing a mole ratio of methyl to phenyl of one or more aromatic compounds in a feed. The process can include providing one or more aromatic methylating agents from a stream to a reaction zone adapted to receive the one or more aromatic methylating agents to form at least one $A7^+$ compound by increasing the mole ratio of methyl to phenyl of at least about 0.1:1 greater than the feed.

The embodiments disclosed herein can provide a process for increasing the mole ratio of methyl to phenyl of one or more aromatic compounds. As a consequence, the process disclosed herein can convert aromatics to higher substituted compounds. Such converted compounds can be higher valued, depending on market conditions, such as para-xylene. Thus, the value of the products produced by the aromatic complex may be increased. Moreover, the embodiments disclosed herein can remove undesired amounts of compounds, such as benzene, from a product, such as a motor fuel product.

In addition, an aromatic alkylating or methylating agent utilized can be one or more non-aromatic compounds or radicals that may be present in the feed of the naphtha and can be provided from one or more fractionation towers within the aromatic complex. Thus, the non-aromatic compounds, such as alkanes or cycloalkanes, may be easily combined with the one or more aromatics to produce higher substituted compounds. In addition, typically less desired compounds such as cumene, indane, and other higher substituted aromatics may also be utilized so that their saturated radicals can alkylate or methylate aromatics, such as benzene, to produce more desired products, such as xylenes. Preferably, the process creates additional substituent methyl groups on the one or more aromatic compounds. Thus, the embodiments disclosed herein can provide an economical and relatively simple system for converting benzene in an aromatic complex.

DEFINITIONS

Figure 1:
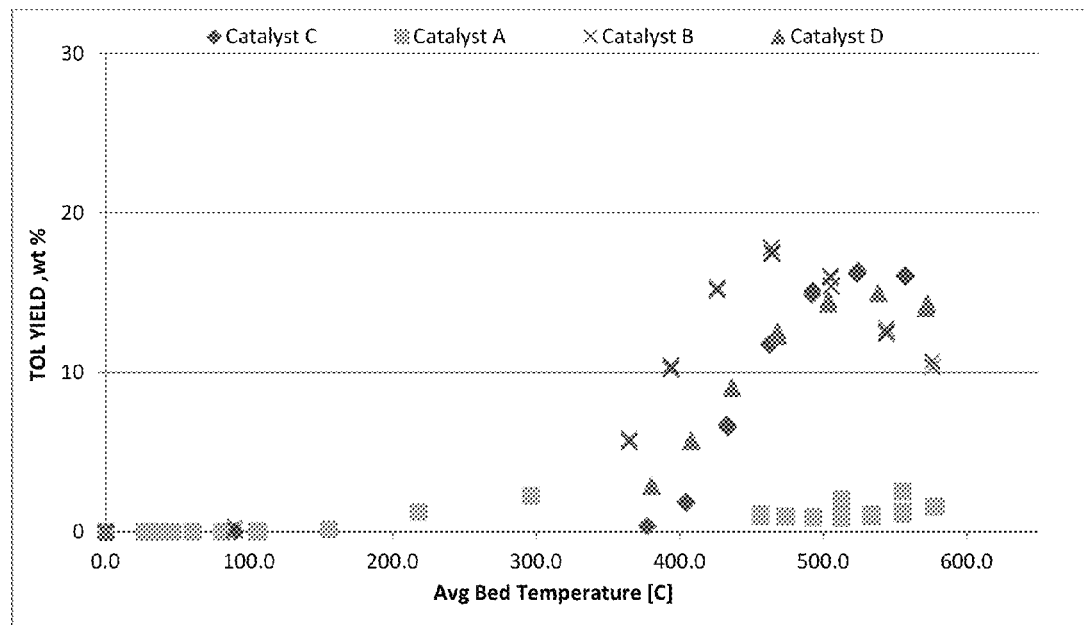
FIG. 1 is a graph showing a comparison of toluene yield as a function of bed temperature between nickel Catalyst A and non-metal zeolite Catalysts B, C, and D in accordance with the Examples provided herein.

As used herein, the term "stream", "feed", or "product" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8 . . . An where "n" represents the number of carbon atoms in the one or more aromatic molecules. Furthermore, a superscript "+" or "−" may be used with an abbreviated one or more hydrocarbons notation, e.g., C3$^+$ or C3$^-$, which is inclusive of the abbreviated one or more hydrocarbons. As an example, the abbreviation "C3$^{+}$" means one or more hydrocarbon molecules of three or more carbon atoms.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "aromatic alkylating agent" means a non-aromatic compound or radical used to produce higher alkyl substituted one or more aromatic compounds. Examples of one or more non-aromatic compounds can include an alkane or a cycloalkane, preferably at least one C2-C8 alkane or C5$^+$ cycloalkane. A non-aromatic radical can mean a saturated group forming a linear or branched alkyl group, a cycloalkyl, or a saturated group fused to an aromatic ring. Aromatic compounds having such non-aromatic radicals can include cumene, indane, and tetralin. The alkylated aromatic compounds can include additional substituent groups, such as methyl, ethyl, propyl, and higher groups. Generally, an aromatic alkylating agent includes atoms of carbon and hydrogen and excludes hetero-atoms such as oxygen, nitrogen, sulfur, phosphorus, fluorine, chlorine, and bromine.

As used herein, the term "aromatic methylating agent" means a non-aromatic compound or radical used to produce higher methyl substituted one or more aromatic compounds. Examples of one or more non-aromatic compounds can include an alkane or a cycloalkane, preferably at least one C2-C8 alkane or C5$^+$ cycloalkane. A non-aromatic radical can mean a saturated group forming a linear or branched alkyl group, a cycloalkyl, or a saturated group fused to an aromatic ring. Aromatic compounds having such non-aromatic radicals can include cumene, indane, and tetralin. The methylated aromatic compounds can include additional substituent methyl groups. Generally, an aromatic methylating agent includes atoms of carbon and hydrogen and excludes hetero-atoms such as oxygen, nitrogen, sulfur, phosphorus, fluorine, chlorine, bromine, and iodine. Such hetero-atom compounds may be referred to as a "methylating agent" and may include compounds such as iodomethane, dimethyl sulfate, dimethyl carbonate, and methyl trifluorosulfonate.

As used herein, the term "radical" means a part or a group of a compound. As such, exemplary radicals can include methyl, ethyl, cyclopropyl, cyclobutyl, and fused ring-groups to an aromatic ring or rings.

As used herein, the term "rich" can mean an amount of at least generally about 50%, and preferably about 70%, by mole, of a compound or class of compounds in a stream.

As used herein, the term "substantially" can mean an amount of at least generally about 80%, preferably about 90%, and optimally about 99%, by mole, of a compound or class of compounds in a stream.

As used herein, the term "metal" can include rhenium, tin, germanium, lead, indium, gallium, zinc, uranium, dysprosium, thallium, chromium, molybdenum, tungsten, iron, cobalt, nickel, platinum, palladium, rhodium, ruthenium, osmium, or iridium.

As used herein, the methyl to phenyl ratio can be calculated as follows:

$$\text{Methyl:Phenyl Mole Ratio} = [\text{Total number of methyls}]/[\text{Total Aromatic Rings}]$$

Where:
Total Aromatic Rings=sum over all i(MS(i)/MW(i)*NR(i))
Total Number of Methyls=sum over all i(MS(i)/MW(i)*ME(i))
  i: Compound Species
  Molecular weight for species i: MW(i)
  Number of aromatic (phenyl) rings for species i: NR(i)
  Number of methyl groups attached onto the phenyl rings of species i: ME(i)
  The mass content of species i, in the feed: MS (i)

Exemplary calculations for various compound species are depicted below:
Single ring aromatics: i: Toluene, NR(i)=1, ME(i)=1; i: Xylene, NR(i)=1, ME(i)=2
Fused aromatic rings: i: Indane, NR(i)=1, ME(i)=0; i: Tetralin, NR(i)=1, ME(i)=0; i: Naphthalene, NR(i)=2, ME(i)=0
Substituents on saturated fused ring: i: 1-methyl-indane and 2-methyl-indane (where one methyl group is attached to the five carbon ring), NR(i)=1, ME(i)=0
Substituents on unsaturated fused ring: i: 4-methyl-indane and 5-methyl-indane (where one methyl group is attached to the phenyl ring), NR(i)=1, ME(i)=1; i: dimethyl 2,6-naphthalene, NR(i)=2, ME(i)=2
Hence, methyl groups are counted when attached to an aromatic group, e.g., phenyl, and not counted when attached to a full or partial, e.g., fused, saturated ring for fused-ring compounds having aromatic and saturated rings.

As used herein, the percent, by mole, of the aromatic ring recovery with respect to the feed can be calculated as follows:

$$\text{Aromatic Ring Recovery} = [\text{Total Aromatic Rings,By Mole,of Product}]/[\text{Total Aromatic Rings,By Mole,of Feed}]*100\%$$

As used herein, the conversion percent, by weight, of C6$^+$ non-aromatic compounds from the feed can be calculated as follows:

$$\text{Conversion} = (((\text{Total Mass Feed } C6^+\text{non-aromatics}) - (\text{Total Mass Product } C6^+\text{non-aromatics}))/(\text{Total Mass Feed } C6^+\text{non-aromatics}))*100\%$$

DETAILED DESCRIPTION

The embodiments provided herein can provide a product having a mole ratio of alkyl, preferably methyl, to phenyl greater than the feed. Particularly, a feed, which may include one or more C8$^-$ hydrocarbons, can be provided to a reaction zone that may increase the methyl substituents on an aromatic ring. Usually, the feed can be provided from one source or multiple sources and include an effective amount of one or more aromatic compounds and one or more non-aromatic compounds absent heteroatoms or aromatic compounds with saturated groups, i.e., one or more aromatic alkylating or methylating agents. Generally, the feed can come from a variety of sources, such as products of reforming, hydrotreating, catalytic or non-catalytic cracking, such as pygas, oligomerizing, condensating, hydroprocessing, coking, vacuum and non-vacuum hydrocarbon distilling, aromatics separating including extracting, and any combination thereof. In addition, at least one of a liquefied petroleum gas, a reformate obtained from cracking, and raffinate from an aromatics extraction zone may be used, alone or in combination, with at least one feed from the sources described above. The non-aromatic compounds and saturated groups can act as an aromatic alkylating, preferably methylating, agent to increase the number of alkyl, preferably methyl, groups on the aromatic compounds. Although one benefit provided by the embodiments discussed herein is increasing the number of methyl groups, it should also be understood that the number of alkyl groups may also be increased as well. Hence, an aromatic methylating agent may also act as an aromatic alkylating agent.

The non-aromatic compounds can include at least one of, independently, one or more cycloalkanes and alkanes, and may comprise at least about 5%, by weight, of the feed. Optionally, the one or more non-aromatic compounds may also include one or more olefins. Usually, the non-aromatic compound includes at least two, preferably three, and even more preferably four carbon atoms and can include at least one of a cycloalkane, which preferably has at least three, desirably five, carbon atoms in the ring, and, independently, a C2-C8 alkane. In other preferred embodiments, the non-aromatic compounds can include one or more C6+ non-aromatic compounds. In yet another preferred embodiment, the one or more C6+ non-aromatic compounds can include at least one of a dimethyl cyclopentane and a methyl cyclopentane. The feed may include at least about 10%, by weight, one or more cycloalkanes, or about 10-about 70%, by weight, one or more cycloalkanes with respect to the weight of the feed. Moreover, the feed may include up to about 50%, by weight, of one or more C2-C5 hydrocarbons with respect to the weight of the feed.

Typically, the feed can include aromatic compounds, such as A6+, as well. The aromatic compounds can include benzene, toluene, one or more xylenes, naphthalene, ethylbenzene, and one or more polynuclear aromatics. The feed can also include naphthalene rings or multiple fused aromatic rings such as polynuclear aromatics (hereinafter may be abbreviated "PNA").

In addition, the aromatic compounds may also include saturated groups. Such compounds may include cumene, indane, and tetralin. As discussed above, the saturated groups may act as an alkylating, preferably methylating, agent.

With respect to the feed, the feed generally includes about 20%, preferably about 35%, by weight, one or more aromatics. In addition, the feed may include about 5%, by weight, benzene with the balance being non-aromatics and with a maximum amount of about 5%, by weight, toluene. In order to obtain a product that can be rich in xylenes, the preferred benzene content in the feed is less than about 75%, by weight, with respect to the weight of the feed. To obtain a product rich in toluene, the benzene content in the feed may be greater than about 75%, by weight, with respect to the weight of the feed. In another embodiment, the feed generally includes at least about 5%, by weight, toluene and at least about 5%, by weight, benzene with a balance of non-aromatics based on the weight of the feed. In yet another preferred embodiment, the feed generally includes benzene in an amount of about 0.5-about 99.5%, by weight, toluene in the amount of about 0.5-about 99.5%, by weight, and non-aromatics in the amount of about 0.5-about 99.5%, by weight, based on the weight of the feed. In yet other embodiments, the feed can include at least about 20%, by weight, benzene with respect to the weight of the feed.

Typically, the feed can comprise about 20-about 95%, by weight, of one or more aromatics, such as benzene, with respect to the weight of the feed. In some other embodiments, the benzene content of the feed can be about 15-about 25%, by weight, with respect to the weight of the feed.

Usually, the feed is substantially absent of methylating agents containing one or more hetero-atoms. As an example, the feed can have less than about 1%, preferably less than about 0.1%, by weight, of one or more methylating agents. Instead, the feed can include an aromatic alkylating agent of one or more saturated compounds or radicals in an amount of at least about 5%, by mole, based on the feed.

The reaction zone, such as an alkyl, preferably methyl, addition zone can operate under any suitable conditions in the liquid or gas phase. Particularly, the reaction zone can operate at a temperature of about 250-about 700° C., preferably about 350-about 550° C., a pressure of about 100-about 21,000 kPa, preferably about 1,900-about 3,500 kPa, a weight hourly space velocity (WHSV) of about 0.1-about 100 $hr^{-1}$, preferably about 2-about 10 $hr^{-1}$, and a hydrogen:hydrocarbon mole ratio of about 0.1:1-about 5:1, preferably about 0.5:1-about 4:1. In another exemplary embodiment, the temperature can be at least about 460° C., desirably at least about 510° C., and more desirably at least about 560° C., a pressure no more than about 7,000 kPa, preferably no more than about 3,500 kPa, and the reaction may occur in a gas phase to facilitate the cracking of non-aromatic hydrocarbons. Alternatively, the temperature can be about 460-about 550° C. At higher temperature and lower pressure conditions, although not wanting to be bound by theory, it is believed that the non-aromatic hydrocarbons and/or saturated groups will form methyl groups instead of alkyl groups. However, it should be understood that at least some alkylation may be occurring where groups such as, e.g. ethyl, propyl, butyl, and higher groups, can be substituted to the one or more aromatic compounds.

Any suitable catalyst may be utilized such as at least one molecular sieve including any suitable material, e.g., alumino-silicate. The catalyst can include an effective amount of the molecular sieve, which can be a zeolite with at least one pore having a 10 or higher member ring structure and can have one or higher dimension. Typically, the zeolite can have a $Si/Al_2$ mole ratio of greater than about 10:1, preferably about 20:1-about 60:1. Preferred molecular sieves can include BEA, MTW, FAU (including zeolite Y in both cubic and hexagonal forms, and zeolite X), MOR, LTL, ITH, ITW, MEL, FER, TON, MFS, IWW, MFI, EUO, MTT, HEU, CHA, ERI, MWW, and LTA. Preferably, the zeolite can be MFI and/or MTW. Suitable zeolite amounts in the catalyst may range from about 1-about 99%, and preferably from about 10-about 90%, by weight. The balance of the catalyst can be composed of a refractory binder or matrix that is optionally utilized to facilitate fabrication, provide strength, and reduce costs. Suitable binders can include inorganic oxides, such as at least one of alumina, magnesia, zirconia, chromia, titania, boria, thoria, phosphate, zinc oxide and silica.

Generally, the catalyst is essentially absent of at least one metal, and typically includes less than about 0.1%, by weight, of total metal based on the weight of the catalyst. Moreover, the catalyst preferably has less than about 0.01%, more preferably has less than about 0.001%, and optimally has less than about 0.0001%, by weight, of total metal based on the weight of the catalyst.

The product produced from the reaction zone can have a mole ratio of methyl to phenyl groups of at least about 0.1:1, preferably greater than about 0.2:1, and optimally greater than about 0.5:1, greater than the feed. The reaction zone can produce an aromatic ring recovery of generally at least about 85%, preferably about 85-about 115%, and optimally about 99-about 101%, by mole, with respect to the feed. Generally, the conversion of one or more $C6^+$ non-aromatic compounds can be greater than about 50%, preferably greater than about 70%, and optimally greater than about 90%, by weight. Thus, the reaction of the one or more $C6^+$ non-aromatic compounds as well as the benzene can minimize the amount of benzene in the resulting product. Typically, the aromatic compounds can receive one or more methyl groups, and optionally other alkyl groups, such as ethyl, propyl, or higher carbon chain substituents.

The product can include one or more $A7^+$ compounds, such as toluene, one or more xylenes, and ethylbenzene. As such, the product may include at least generally about 2% xylenes, preferably about 5%, and optimally about 10%, by weight, of one or more xylenes. In addition, the para-xylene percent of the total xylenes can be at least about 20%, preferably at least about 23%, and optimally at least about 23.8%. In other preferred embodiments, the feed can include at least 0.5%, by weight, benzene with respect to the weight of the feed and produce a product that has less than about 0.5%, by weight, benzene with respect to the weight of the product. In yet other preferred embodiments, the feed can contain greater than about 0.5%, by weight, benzene with respect to the weight of the feed and have a product that is less than about 20%, by weight, benzene with respect to the weight of the product. In still other preferred embodiments, the benzene content in the product can be reduced to less than about 20%, by weight, and preferably less than about 0.5%, by weight, with respect to the weight of the product. Any benzene that is present in the feed can be substituted with a saturated group present in one or more other aromatic compounds, such as polynuclear aromatics, in order to obtain a product that may be rich in methyl group substituted aromatics, including substituted one or more naphthalenes and other polynuclear aromatics.

What is more, the reaction zone can convert other compounds, such as one or more olefin compounds, one or more sulfur-containing compounds and one or more halide-containing compounds. Particularly, about 80%, by weight, of the one or more $C3^+$ olefins can be converted with respect to the feed. Preferably, sulfur-containing compounds, such as thiophene and thiophene derivatives, one or more $C3^+$ mercaptans, as well as one or more heavier halides can be converted by at least about 95%, by weight, with respect to the feed. In addition, other compounds may also be converted such as one or more oxygen-containing compounds, e.g., one or more tertiary butyl alcohol compounds.

Generally, a downstream process can utilize one or more products, such as benzene, para-xylene, meta-xylene and ortho-xylene, of the embodiments disclosed herein. Particularly, para-xylene, upon oxidation, can yield terephthalic acid used in the manufacture of textiles, fibers, and resins. Moreover, para-xylene can be used as a cleaning agent for steel and silicon wafers and chips, a pesticide, a thinner for paint, and in paints and varnishes. Meta-xylene can be used as an intermediate to manufacture plasticizers, azo dyes, wood preservatives and other such products. Ortho-xylene can be a feedstock for phthalic anhydride production. Additionally, xylenes generally may be used as a solvent in the printer, rubber, and leather industries. Moreover, the methyl groups on xylenes can be chlorinated for use as lacquer thinners. Benzene can be used as a feed to make cyclohexane, which in turn may be used to make nylons. Also, benzene can be used as an intermediate to make styrene, ethylbenzene, cumene, and cyclohexane. Moreover, smaller amounts of benzene can be used to make one or more rubbers, lubricants, dyes, detergents, drugs, explosives, napalm, and pesticides.

The following examples are intended to further illustrate the subject embodiments. These illustrations of embodiments of the invention are not meant to limit the claims of this invention to the particular details of these examples. These examples are based on engineering calculations and actual operating experience with similar processes.

Example 1

All three runs are simulated at generally the same conditions, such as at a pressure of about 2,760 kPa, except a first run is at a temperature of 481.4° C., a second run is at a temperature of 511.3° C., and a third run at a temperature of 568.5° C. The composition in percent, by weight, of the feed and product runs as well as the results are depicted in Table 1 below:

TABLE 1

|  | FEED | PRODUCT RUN 1 | PRODUCT RUN 2 | PRODUCT RUN 3 |
|---|---|---|---|---|
| C1 | 0.00 | 7.8 | 14.9 | 24.6 |
| C2 | 0.00 | 10.8 | 17.5 | 23.0 |
| C3 | 0.12 | 16.1 | 9.9 | 2.3 |
| n-C4 | 0.21 | 1.9 | 0.6 | 0.2 |
| i-C4 | 0.90 | 1.9 | 0.8 | 0.2 |
| n-C5 | 5.43 | 1.0 | 0.0 | 0.0 |
| i-C5 | 5.96 | 1.7 | 0.2 | 0.0 |
| C6-C8 non-aromatics | 36.89 | 4.4 | 0.9 | 0.4 |
| XY | 0.03 | 4.2 | 6.1 | 5.4 |
| TOL | 0.98 | 14.6 | 19.4 | 18.3 |
| EB | 0.00 | 3.9 | 2.5 | 1.2 |
| BZ | 49.03 | 27.5 | 22.5 | 19.7 |
| $A9^+$ | 0.44 | 4.3 | 4.6 | 4.6 |
| TOTAL | 100.00 | 100.0 | 100.0 | 100.0 |
| Methyl:phenyl mole ratio | 0.02 | 0.4 | 0.6 | 0.6 |
| Benzene conversion % | 0.00 | 44.0 | 54.1 | 59.8 |
| C5 non-aromatic conversion % | 0.00 | 76.9 | 98.4 | 99.8 |
| Average Rx Temp ° C. | 0.00 | 481.4 | 511.3 | 568.5 |
| C6-C8 non-aromatic conversion % | 0.00 | 88.2 | 97.5 | 99.1 |

As depicted, each product for each run can have a methyl:phenyl mole ratio of at least about 0.1:1 greater than the feed, while the products of runs 2 and 3 at an average reaction temperature of at least 511° C. exceed a conversion of 90% for C6-C8 non-aromatics.

Example 2

As a comparative example, a nickel catalyst described by U.S. Pat. No. 2,168,590 to Taylor was reproduced. A nickel catalyst in accordance with Taylor was prepared by first forming R-9 alumina, commercially available from UOP LLC, by oil dropping an aluminum hydroxychloride solution having an Al/Cl wt ratio of 1.19. They were then neutralized and gelled with HMT and then pressure aged. Next, the spheres were washed until they were Cl-free and then dried. Finally the spheres were calicined in air at 650° C. for 4 hours to produce a spherical support of gamma-alumina with ABD=0.5 g/cc.

Nickel was then impregnated into the gamma-alumina spherical supports by rotary impregnation with an aqueous solution of nickel (II) nitrate. The impregnation was accomplished with a 1:1 solution:base volume ratio. The support was added to a jacketed glass evaporator jar, immediately followed by the metal solution. The nickel catalyst is referred to as Catalyst A and the composition is provided in Table 2 below.

Example 3

To provide a comparison between the catalyst based on Taylor and catalysts as described herein, catalysts as described in the present application were also tested to show the difference between the process using catalysts in accordance with the current application and the catalyst of Taylor.

For comparison, different catalysts were tested that included either MFI, MTW, and MOR zeolite. Each of the catalysts was made by extruding a dough of the particular zeolite by known methods that has been NH4-exchanged and peptized with HNO3 Catapal alumina to make a final catalyst having between 70-80% zeolite. The extrudates were dried and subsequently calcined at between 540-550° C. for 2-3 hours in air. The final wt-% of the components in the catalysts was determined based on the wt-% of the components added during formation of the catalysts.

Catalyst B was formed as described above using an MFI zeolite and was 75 wt-% MFI with the balance being Al2O3 binder.

Catalyst J was formed nominally by the same method as that described above for Catalyst B using an MFI zeolite and was 75 wt-% MFI with the balance being Al2O3 binder. However, additional steam was added during the calcination step of Catalyst J.

Catalyst C was formed as described above using an MTW zeolite and was 80 wt-% MTW with the balance being Al2O3 binder.

Catalyst D was formed as described above using an MOR zeolite and was 75 wt-% MOR with the balance being Al2O3 binder.

For further comparison, Catalyst E including UZM-8 was prepared according to the method described above for preparing Catalysts B-D using a UZM-8 zeolite. Catalyst E was 70 wt-% UZM-8 with the balance being Al2O3 binder.

Example 4

Catalysts F, G, and H were modified to include rhenium. To prepare Catalyst F, a composition prepared in accordance with Catalyst J described above was modified to include 0.15 wt-% rhenium. To prepare Catalyst G, a composition prepared in accordance with Catalyst C described above was modified to include 0.15 wt-% rhenium. To prepare Catalyst H, a composition prepared in accordance with Catalyst E described above was modified to include 0.15 wt-% rhenium. Catalyst I was modified to include platinum. To prepare Catalyst I, a composition prepared in accordance with Catalyst B described above was modified to include 100 ppm platinum. The amount of metal on the metal-containing catalysts was added with the same impregnation procedure described earlier and cited below again. The amount of metal added to the impregnation solution was adjusted to provide the target weight percent of metal on the final calcined catalyst on a volatile free basis. One can use inductive coupled plasma (ICP) to verify the metal content on the final catalyst sample, which was done for at least one of the samples in this case. However, it is expected that with impregnation all of the metal in the solution ends up on the catalyst so that the final metal levels are expected to be very close to the target levels for all of the metal containing catalysts.

The metal-supported catalysts were made by rotary impregnation of the corresponding metal-free catalysts with aqueous solutions of the following metal compounds. Catalysts F, G, and H were formed using perrhenic acid (HReO4). Catalyst I was made using Chloroplatinic acid (CPA, H2PtCl6). The impregnations were done with a 1:1 solution:base volume ratio. The metal free catalyst was added to a jacketed glass evaporator jar, immediately followed by the metal solution. The support was cold-rolled for 1 hour, then steam was introduced to the jacket of the evaporator jar to begin the drying step. When the impregnated support was dry, the steam was shut off. Each sample was then calcined in a tray oven at 500° C. for 2 hours under air purge.

The approximate compositions of each of the Catalyst samples described above are provided in Table 2 below.

TABLE 2

Compositions of the tested catalyst samples.

| Catalyst | Zeolite | Metal | Binder |
|---|---|---|---|
| A | None | 0.3% Ni | Gamma-alumina |
| B | 75 wt % MFI | None | $Al_2O_3$ |
| C | 80 wt % MTW | None | $Al_2O_3$ |
| D | 75 wt % MOR | None | $Al_2O_3$ |
| E | 70 wt % UZM-8 | None | $Al_2O_3$ |
| F | 75 wt % MFI | 0.15 wt % Re | $Al_2O_3$ |
| G | 80 wt % MTW | 0.15 wt % Re | $Al_2O_3$ |
| H | 70 wt % UZM-8 | 0.15 wt % Re | $Al_2O_3$ |
| I | 75 wt % MFI | 100 ppm Pt | $Al_2O_3$ |
| J | 75 wt % MFI | None | $Al_2O_3$ |

Example 5

Each of the Catalysts A-J described above was tested according to the following procedure. For each catalyst, 15 grams of the catalyst was loaded in a standard fixed bed reactor with a thermowell, capable of measuring temperatures in fixed locations inside the catalyst bed. The hydrocarbon (HC) feed was nominally 50% by weight Benzene and the balance n-pentane.

The catalyst was pretreated under hydrogen flow at Atmospheric pressure. The hydrogen flow rate was kept equivalent to 4 molar H2 to 1 mole of the HC feed at the test conditions, further described below. The heat up-rate was maintained at 5° C. per minute. Non-metal containing catalysts were heated to 550° C. and held for 2 hours. Metal containing catalysts were heated to 530° C. and held for 2 hours.

After the pretreatment phase, the pressure was adjusted to 400 psig. $H_2$ flow was still maintained at an equivalent of 4 molar $H_2$ to 1 mole of the HC feed. Catalyst bed temperatures were lowered to 530° C. for non-metal catalysts and 510° C. for metal containing catalysts. The HC feed was then introduced at 2.5 WHSV. Heater controls were adjusted to increase or decrease the average catalyst bed temperature, to increase or decrease feed conversion, and to generate the performance curves provided.

The reactor effluent composition was generated by combining the compositions and mass flows measured of two product streams recovered as gas and liquid downstream of the reactor. The total reactor effluent hydrocarbon composition was then obtained by normalizing the merged hydrocarbon component mass flows to 100%.

The liquid product and gas product compositions were obtained using a single on-line GC system, employing two columns and two distinct sampling systems, one for gas and one for the liquid sample. The on-line GC measured gas and liquid compositions approximately once for every one hour during the test. Specifications of the GC include:

Oven: 40° C., 4 minutes, 5° C./min to 220° C., hold 10 minutes

Columns: 50 m×0.2 mm PONA 0.5 uM film for both gas and liquid sample systems

Carrier gas: $H_2$ @ 45 cm/sec avg. linear velocity

Split Ratio: 100:1

Liquid sampling: 0.5 uL Valco liquid sampling valve

Gas Sampling: 250 uL Valco gas sampling valve

Liquid analysis with FID detector, relative response factors for Wt. %

Gas analysis with TCD detector, externally calibrated for absolute Response Factors in mol %, Hydrogen=100−sum of all HCBN's The gas stream was converted into moles component, then grams component, then added to the mass of each component from the liquid analysis to come up with a overall effluent Wt. % distribution.

Example 6

Figure 2:
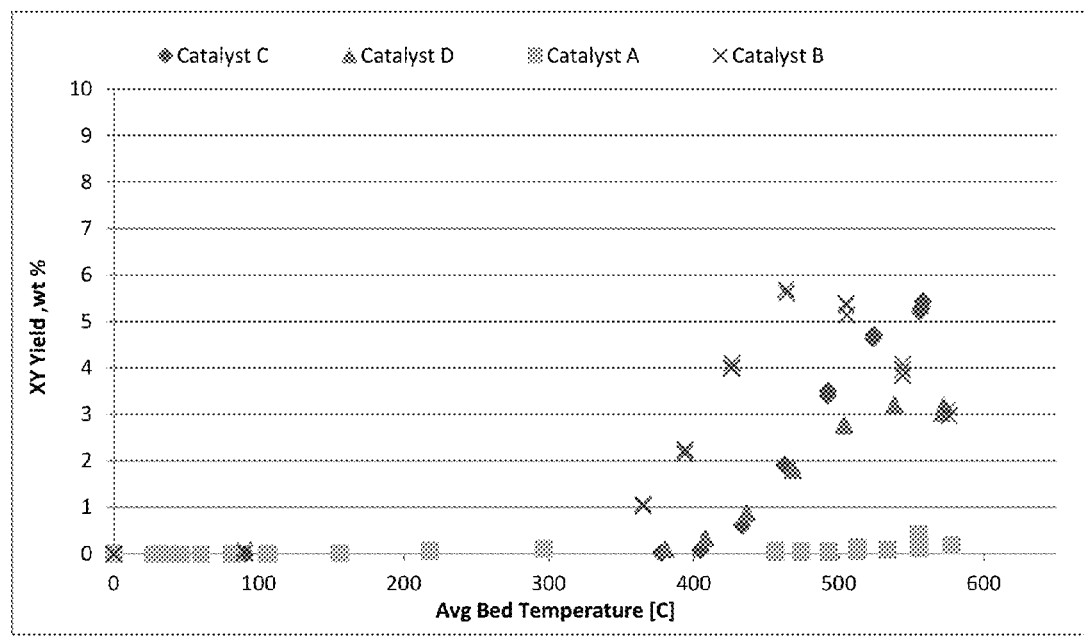
FIG. 2 is a graph showing a comparison of xylene yield as a function of bed temperature between nickel Catalyst A and non-metal zeolite Catalysts B, C, and D in accordance with the Examples provided herein.
Figure 3:
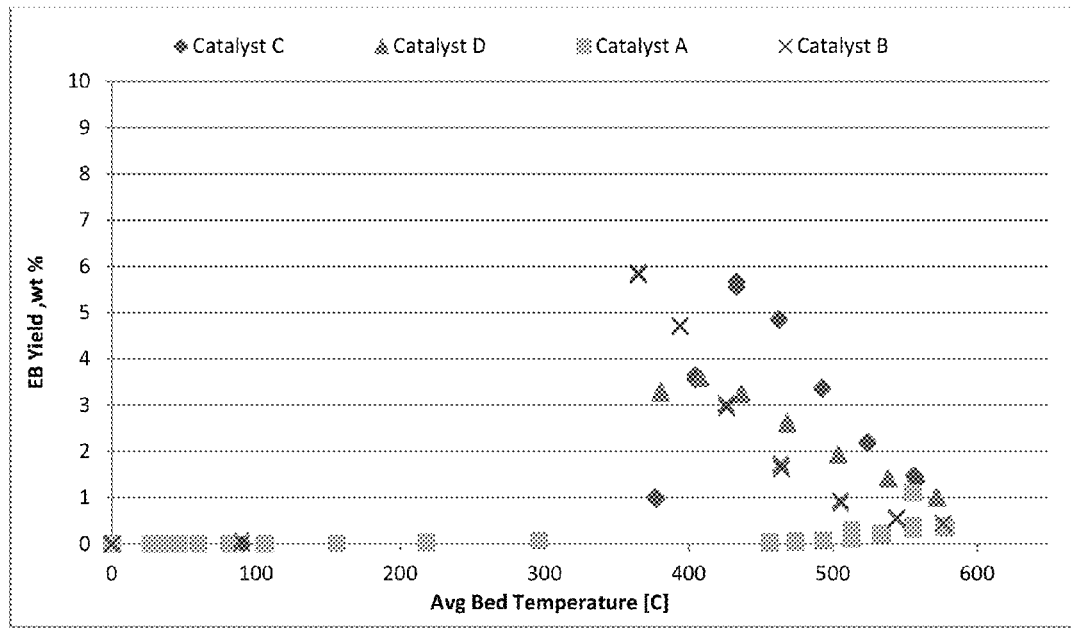
FIG. 3 is a graph showing a comparison of ethylbenzene yield as a function of bed temperature between nickel Catalyst A and non-metal zeolite Catalysts B, C, and D in accordance with the Examples provided herein.
Figure 4:
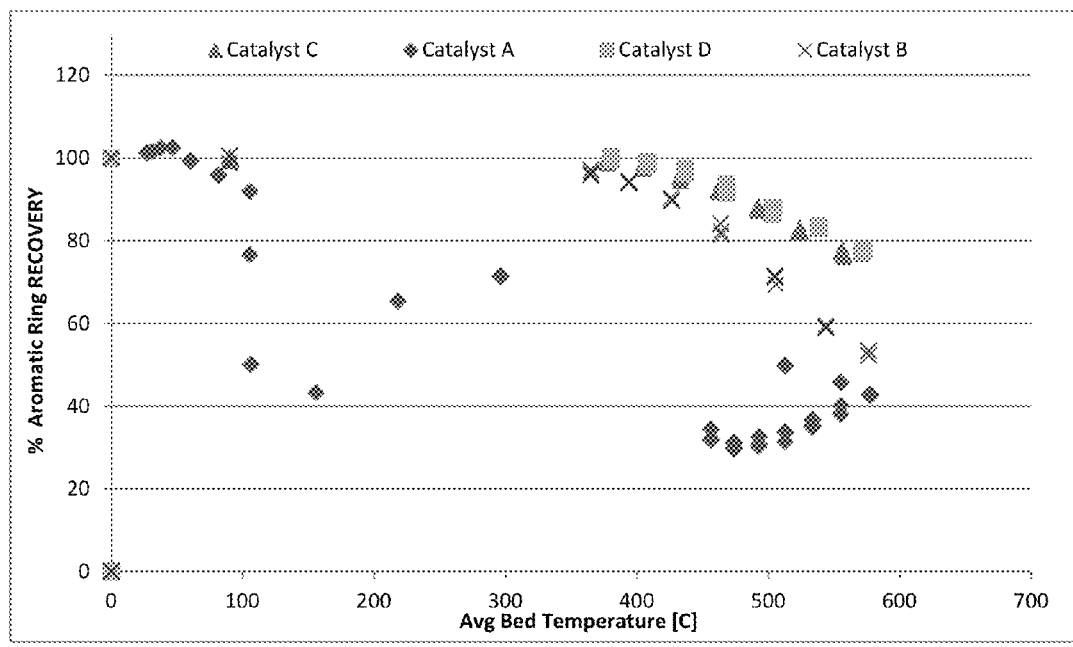
FIG. 4 is a graph showing a comparison of aromatic ring recovery as a function of bed temperature between nickel Catalyst A and non-metal zeolite Catalysts B, C, and D in accordance with the Examples provided herein.
Figure 5:
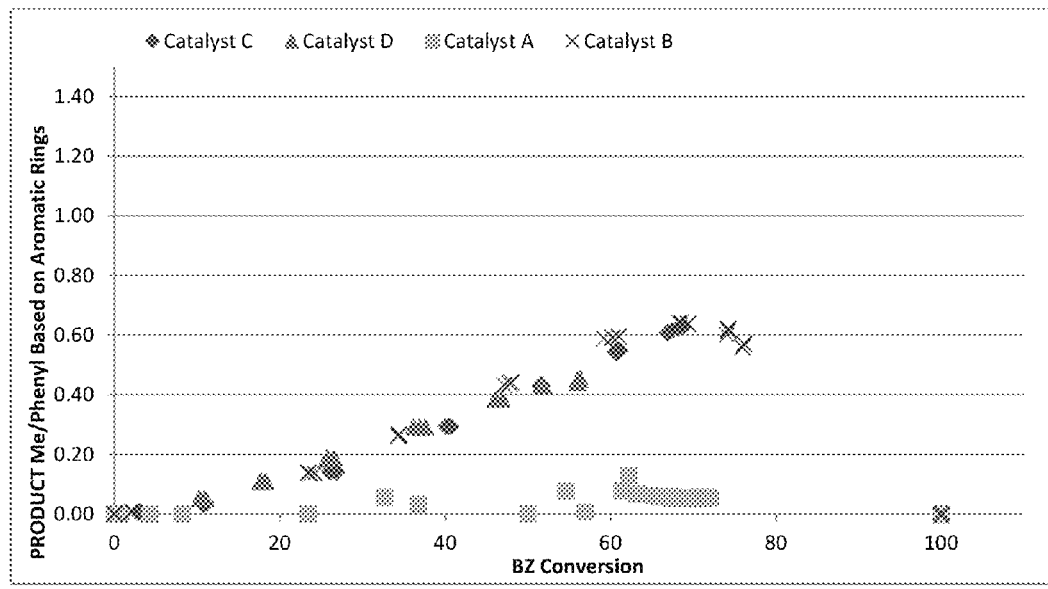
FIG. 5 is a graph showing a comparison of the methyl to phenyl ratio as a function of benzene conversion between nickel Catalyst A and non-metal zeolite Catalysts B, C, and D in accordance with the Examples provided herein.

The attached Figures provide comparative results of the catalyst testing. FIGS. 1-5 compare the nickel catalyst made in accordance with Taylor to the metal free zeolite catalysts made in accordance with the present application. FIGS. 1-3 show that Catalysts B, C, and D provide much better selectivity to toluene and xylenes than the nickel containing Catalyst A, while the nickel containing Catalyst A shows little or no selectivity to toluene, xylenes, or ethylbenzene across the tested catalyst bed temperatures. The current application also describes how to calculate the percentage of aromatic ring recovery in paragraph 18 and the methyl to phenyl mole ratio in paragraph 17. The aromatic ring recovery and the methyl to phenyl mole ratio were calculated for each of the test runs. The zeolite catalysts B, C, and D provide better aromatic ring recovery as compared to the nickel Catalyst A, as illustrated in FIG. 4. Finally, as shown in FIG. 5, the zeolite catalysts provide a much higher methyl to phenyl ratio.

Figure 6:
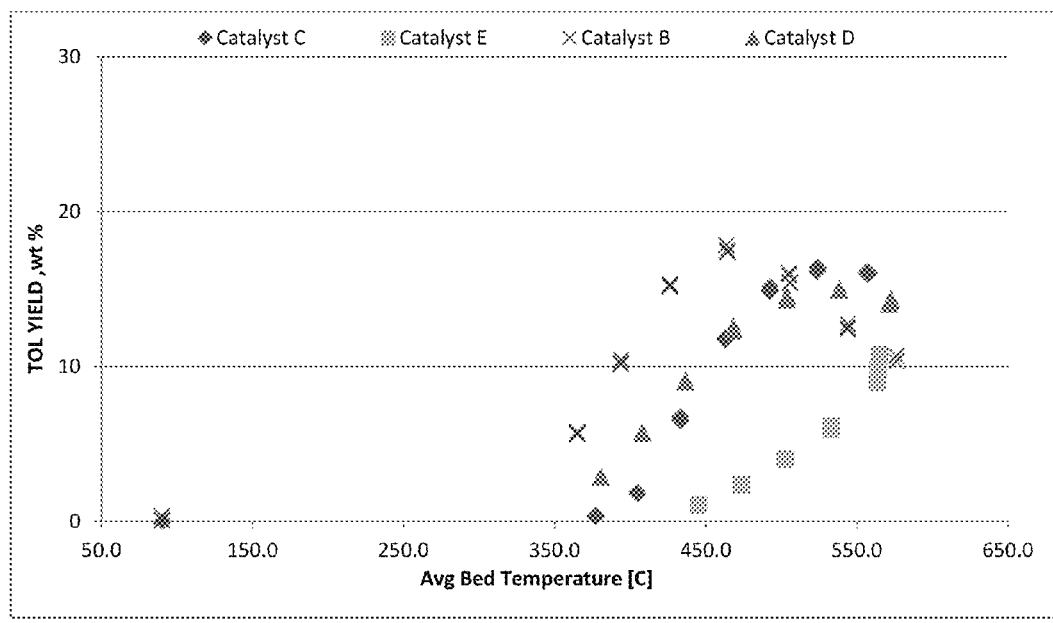
FIG. 6 is a graph showing a comparison of toluene yield as a function of bed temperature between non-metal catalysts B, C, D, and E in accordance with the Examples provided herein.
Figure 7:
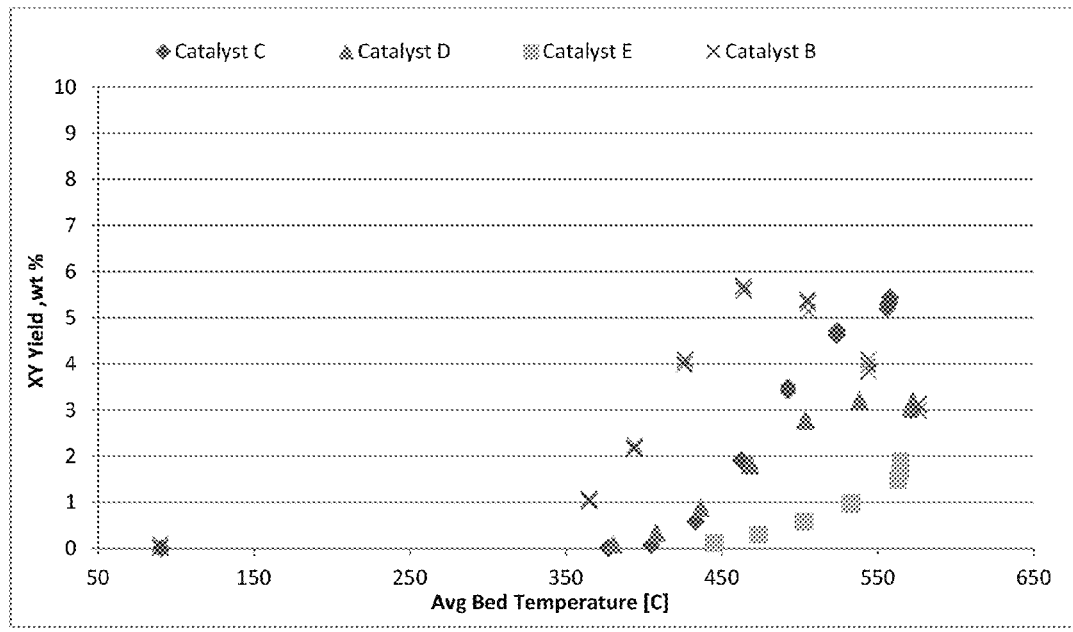
FIG. 7 is a graph showing a comparison of xylene yield as a function of bed temperature between non-metal catalysts B, C, D, and E in accordance with the Examples provided herein.
Figure 8:
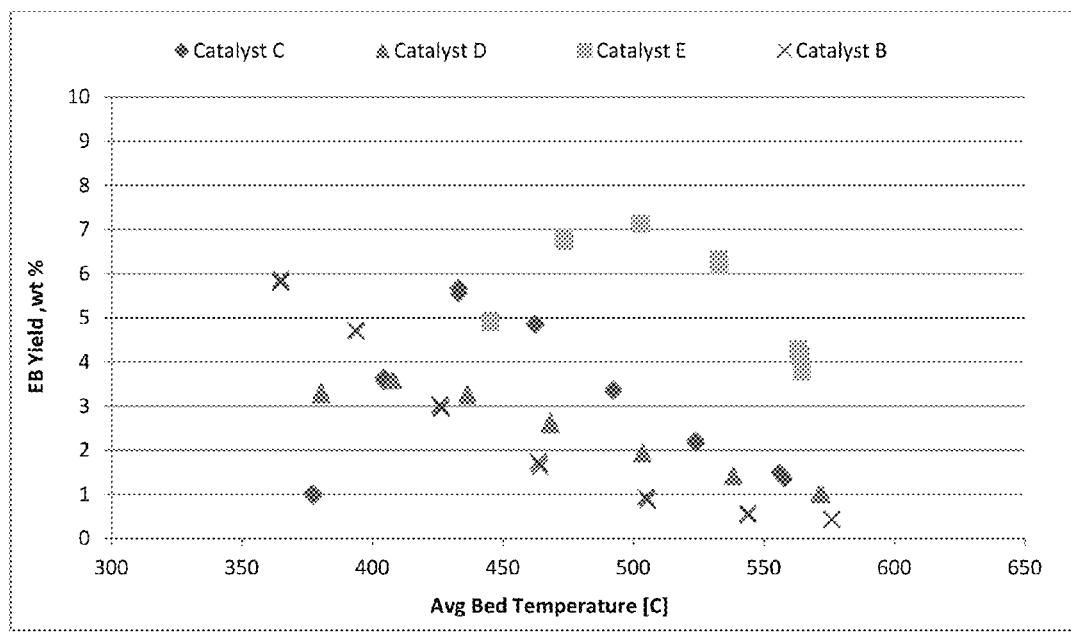
FIG. 8 is a graph showing a comparison of ethylbenzene yield as a function of bed temperature between non-metal catalysts B, C, D, and E in accordance with the Examples provided herein.
Figure 9:
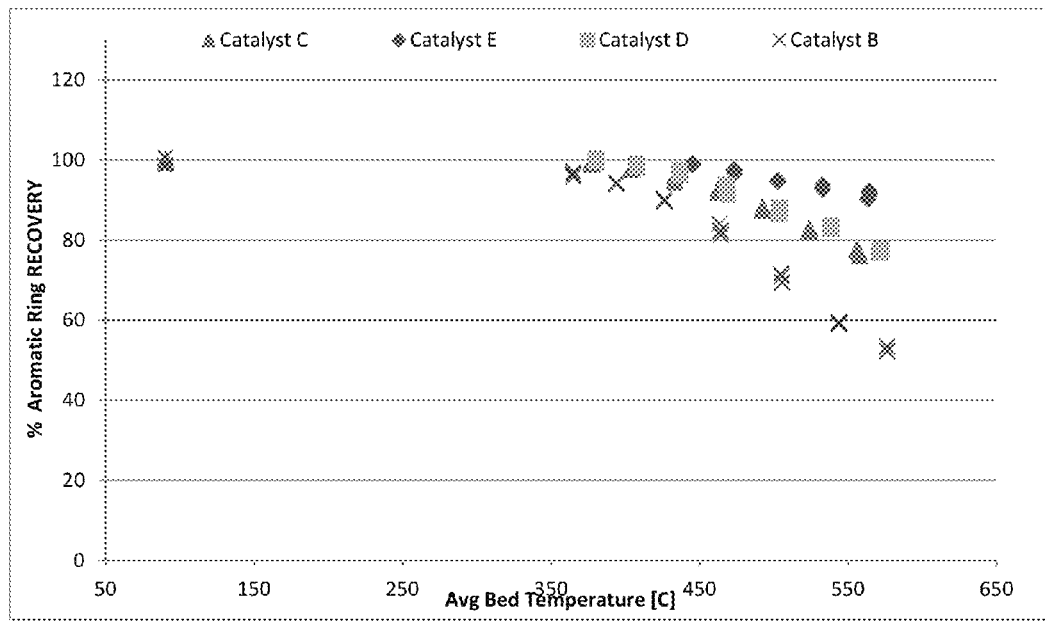
FIG. 9 is a graph showing a comparison of aromatic ring recovery as a function of bed temperature between non-metal catalysts B, C, D, and E in accordance with the Examples provided herein.
Figure 10:
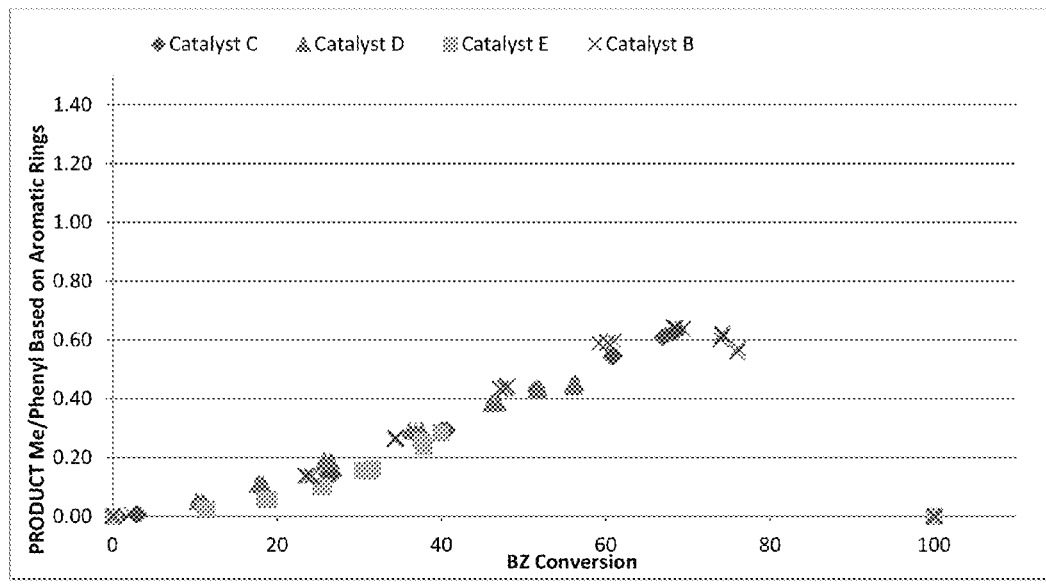
FIG. 10 is a graph showing a comparison of methyl to phenyl ratio as a function of benzene conversion between non-metal catalysts B, C, D, and E in accordance with the Examples provided herein.

FIGS. 6-10 compare the test results of the zeolite catalysts prepared in accordance with the present application. FIGS. 6-8 show that while all of the tested zeolite catalysts are selective to the production of toluene, xylenes, and ethylbenzene, the MFI, MOR, and MTW catalysts provided better selectivity than the UZM-8 catalyst for the production of toluene and xylenes.

Figure 11:
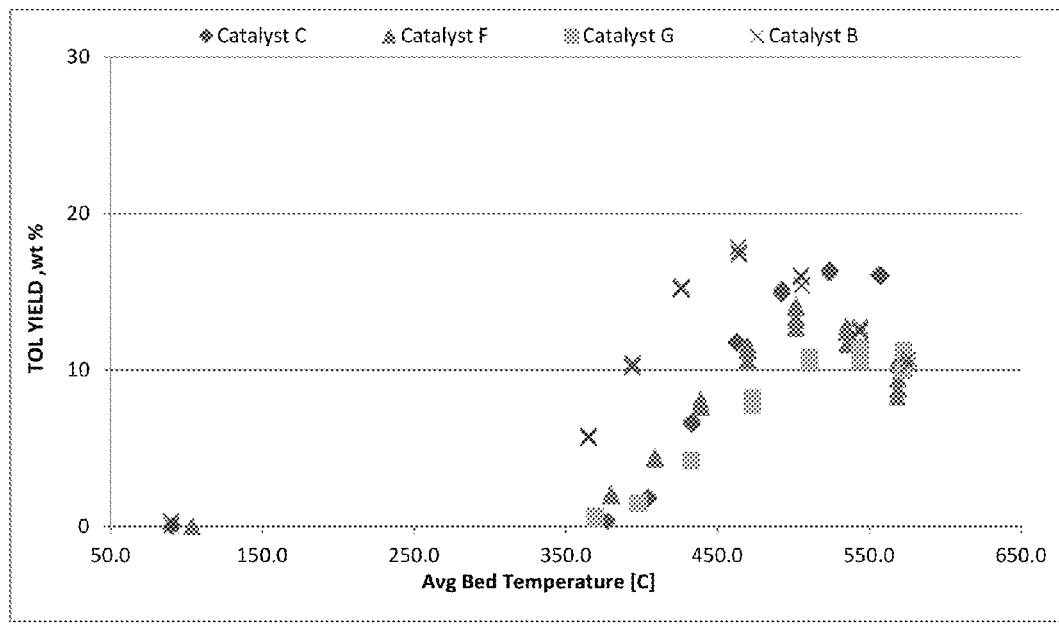
FIG. 11 is a graph showing a comparison of toluene yield versus bed temperature between metal containing and non-metal containing MFI and MTW zeolite catalysts in accordance with the Examples provided herein.
Figure 12:
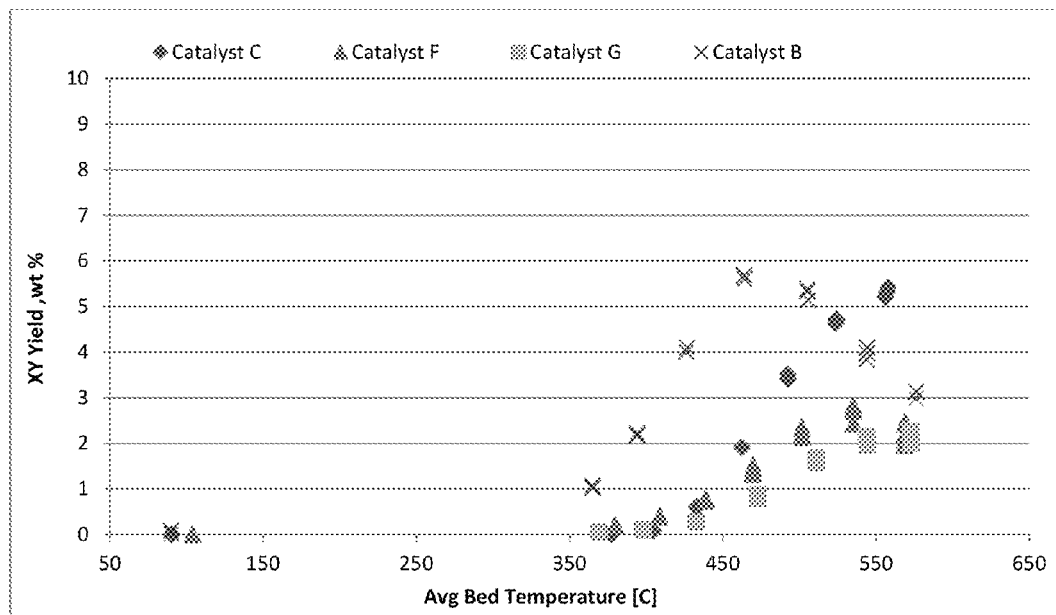
FIG. 12 is a graph showing a comparison of xylene yield versus bed temperature between metal containing and non-metal containing MFI and MTW zeolite catalysts in accordance with the Examples provided herein.
Figure 13:
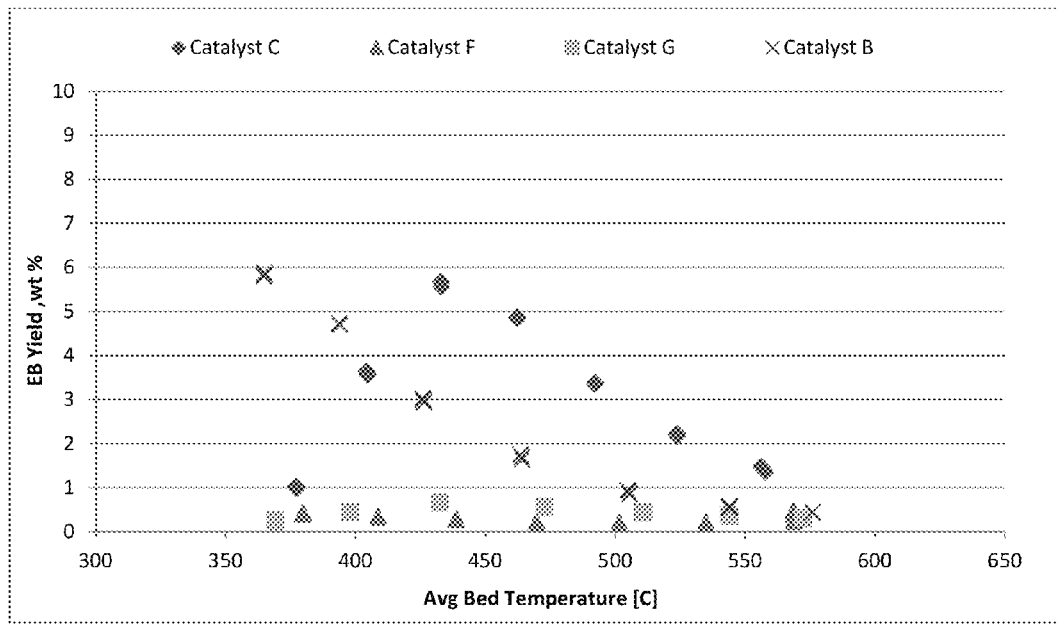
FIG. 13 is a graph showing a comparison of ethylbenzene yield versus bed temperature between metal containing and non-metal containing MFI and MTW zeolite catalysts in accordance with the Examples provided herein.
Figure 14:
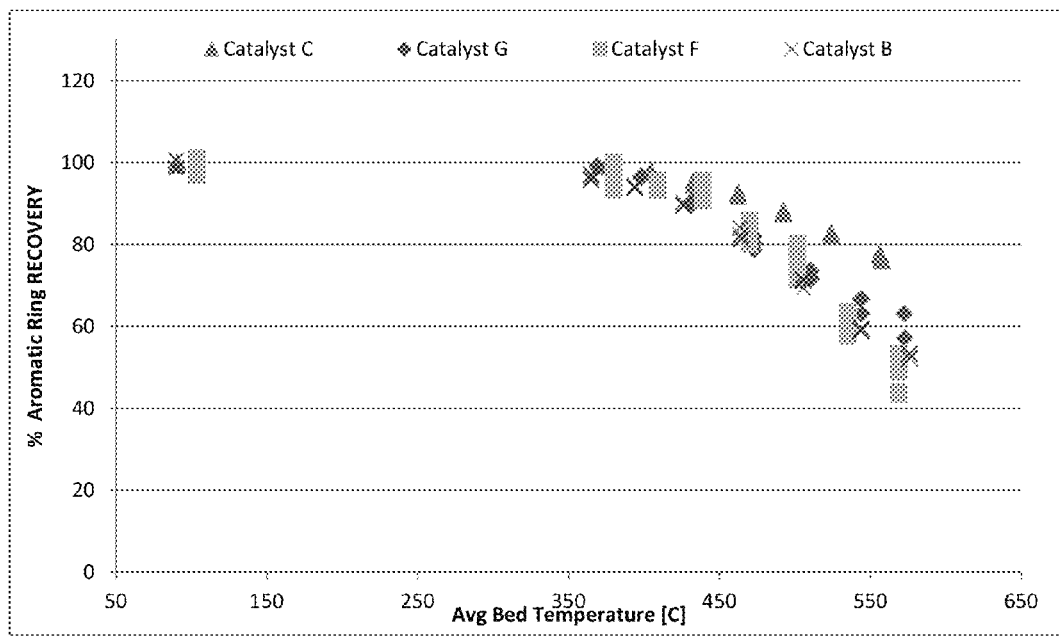
FIG. 14 is a graph showing a comparison of aromatic ring recovery versus bed temperature between metal containing and non-metal containing MFI and MTW zeolite catalysts in accordance with the Examples provided herein.
Figure 15:
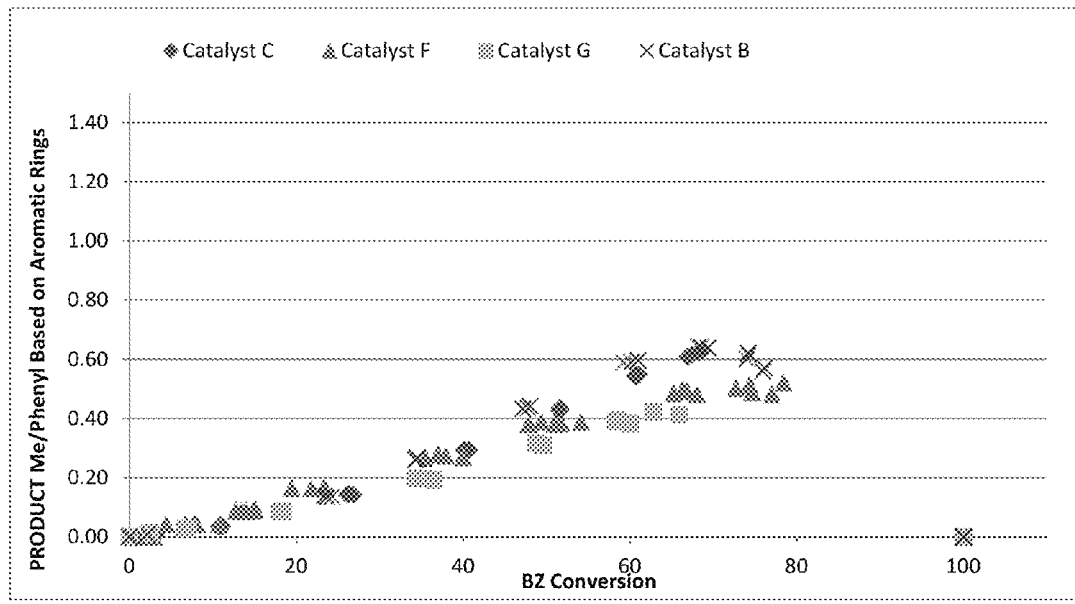
FIG. 15 is a graph showing a comparison of methyl to phenyl ratio versus benzene conversion between metal containing and non-metal containing MFI and MTW zeolite catalysts in accordance with the Examples provided herein.

FIGS. 11-15 compare the test results of the Catalysts B, C, F, and G to illustrate the effect that including a hydrogenation/dehydrogenation metal has on the catalyst activity and selectivity. FIGS. 11 and 12 show that Catalyst F containing MFI and rhenium have lower selectivity to toluene, xylene, and ethylbenzene than the non-rhenium containing MFI Catalyst B. Similarly, the figures show that Catalyst G containing MTW and rhenium has lower selectivity to toluene, xylene, and ethylbenzene than the non-rhenium containing MTW Catalyst C.

Figure 16:
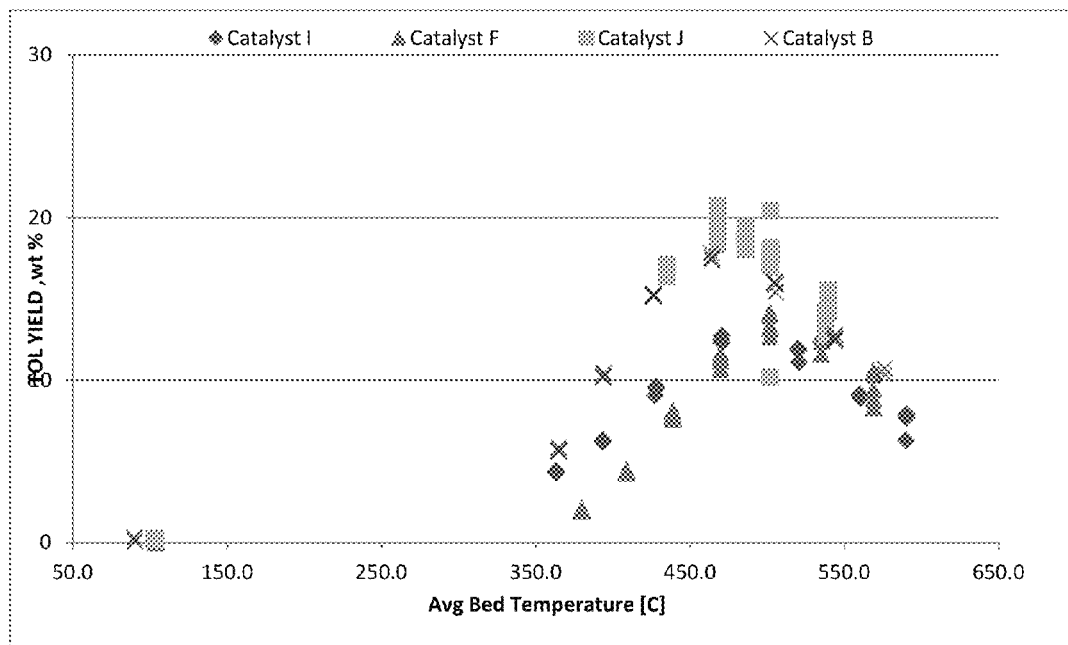
FIG. 16 is a graph showing a comparison of toluene yield as a function of bed temperature between non-metal, platinum containing, and rhenium containing MFI zeolite catalysts in accordance with the Examples provided herein.
Figure 17:
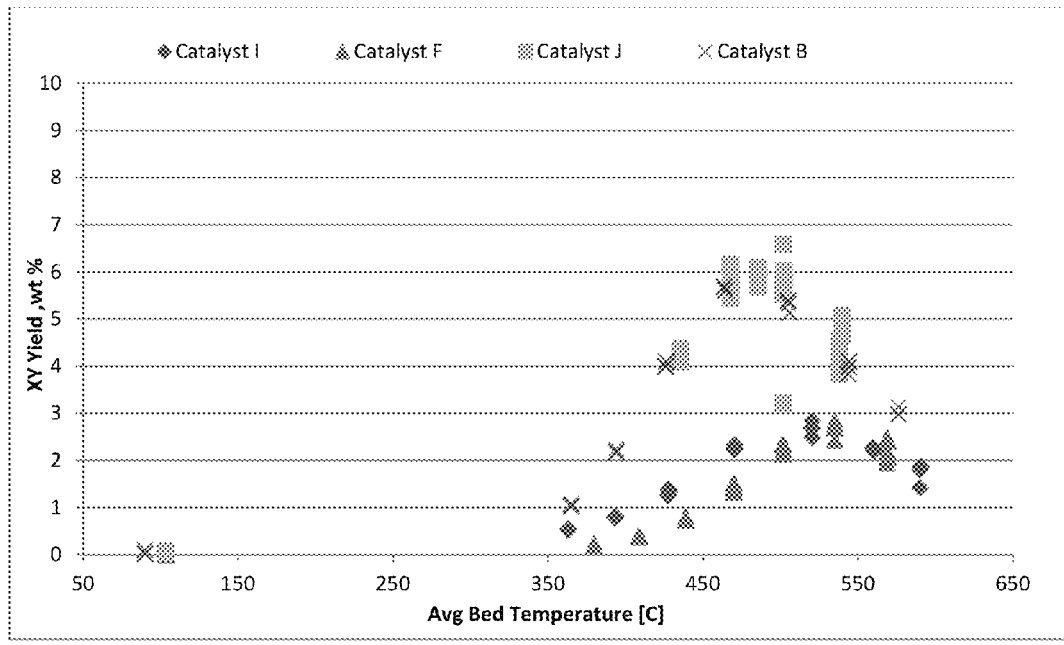
FIG. 17 is a graph showing a comparison of xylene yield as a function of bed temperature between non-metal, platinum containing, and rhenium containing MFI zeolite catalysts in accordance with the Examples provided herein.
Figure 18:
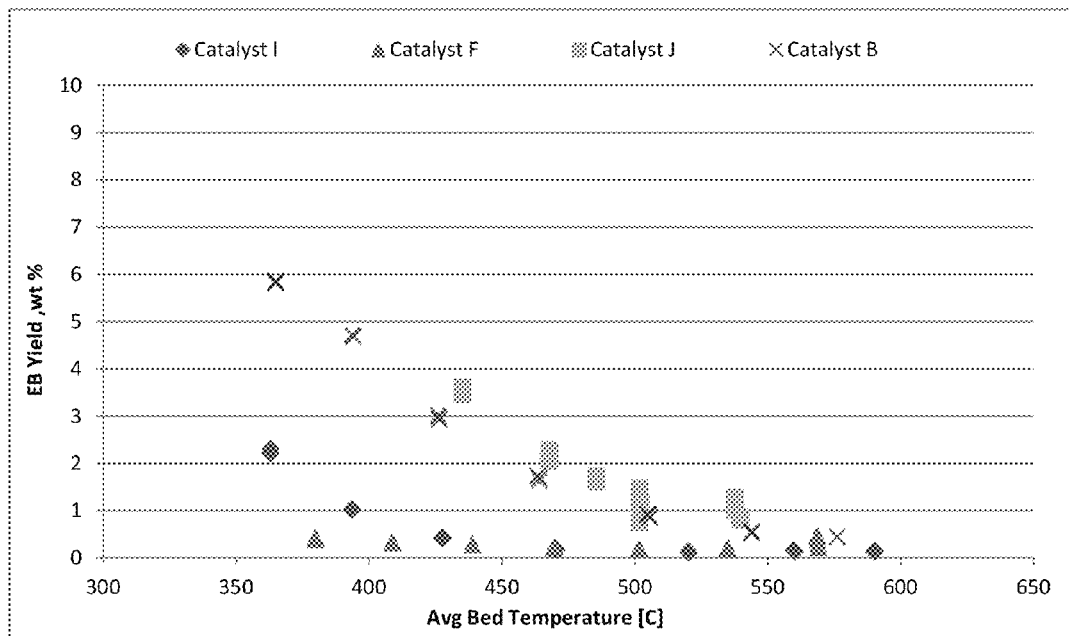
FIG. 18 is a graph showing a comparison of ethylbenzene yield as a function of bed temperature between non-metal, platinum containing, and rhenium containing MFI zeolite catalysts in accordance with the Examples provided herein.
Figure 19:
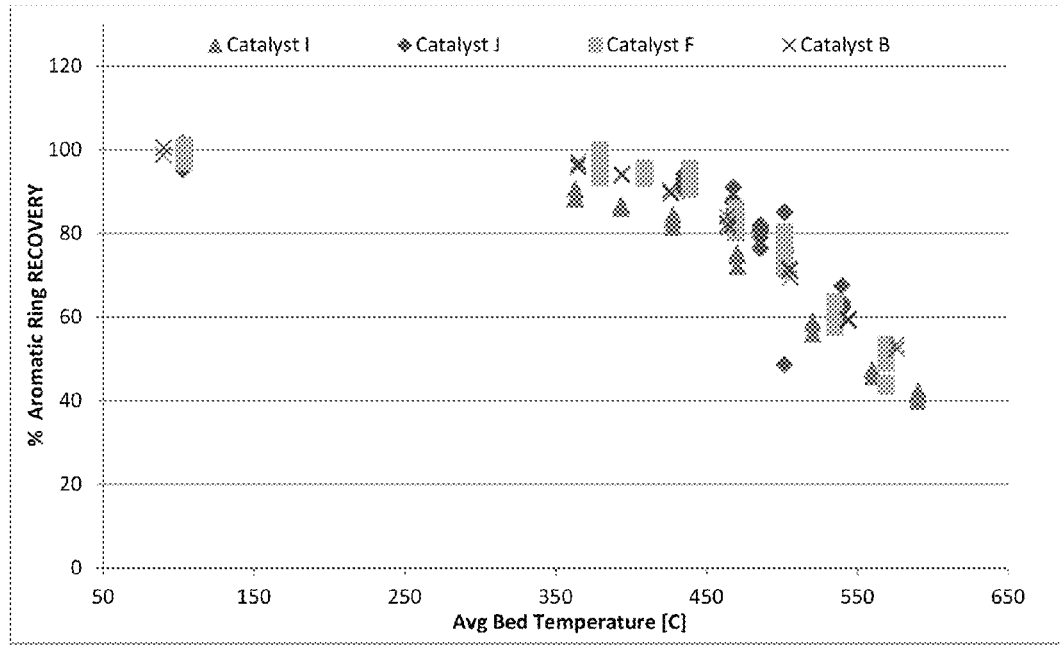
FIG. 19 is a graph showing a comparison of aromatic ring recovery as a function of bed temperature between non-metal, platinum containing, and rhenium containing MFI zeolite catalysts in accordance with the Examples provided herein.
Figure 20:
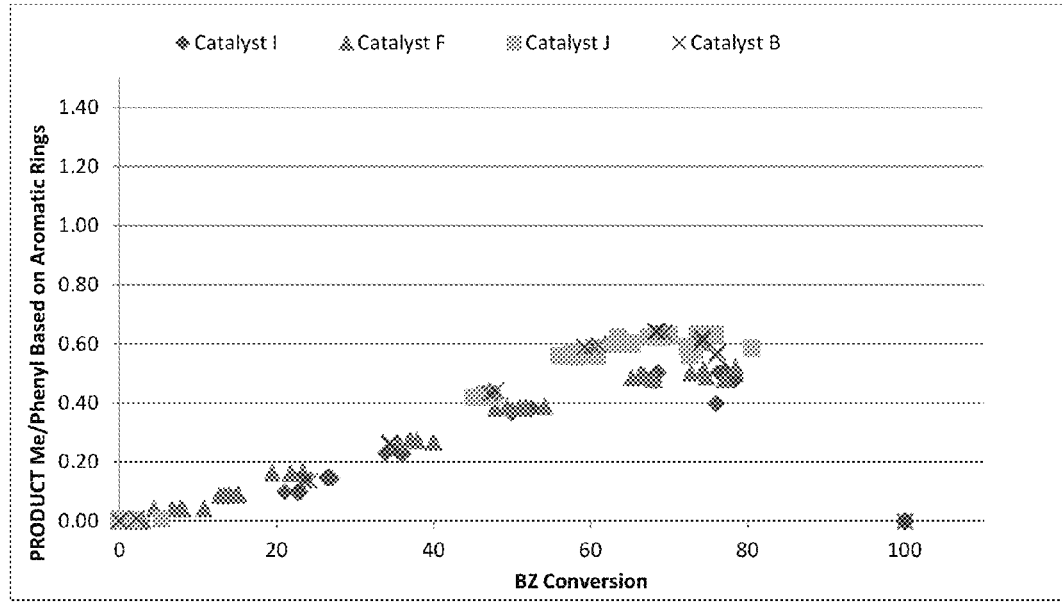
FIG. 20 is a graph showing a comparison of methyl to phenyl ratio as a function of benzene conversion between non-metal, platinum containing, and rhenium containing MFI zeolite catalysts in accordance with the Examples provided herein.

FIGS. 16-20 provide further comparison between metal and non-metal containing catalysts and compare the test results of Catalysts B, F, I, and J, which each contains MFI zeolite. FIGS. 16-18 show that both metal containing Catalyst F containing rhenium and catalyst I containing platinum have poorer selectivity than the non-metal containing MFI Catalysts B and J.

Figure 21:
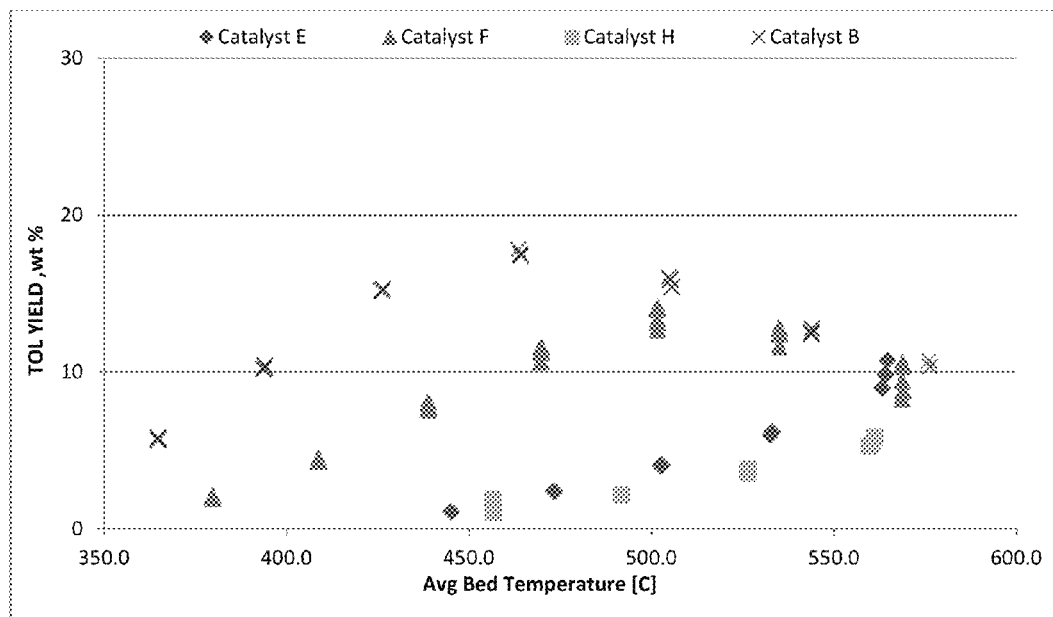
FIG. 21 is a graph showing a comparison of toluene yield as a function of bed temperature between rhenium and non-rhenium containing UZM-8 and MFI zeolite catalysts in accordance with the Examples provided herein.
Figure 22:
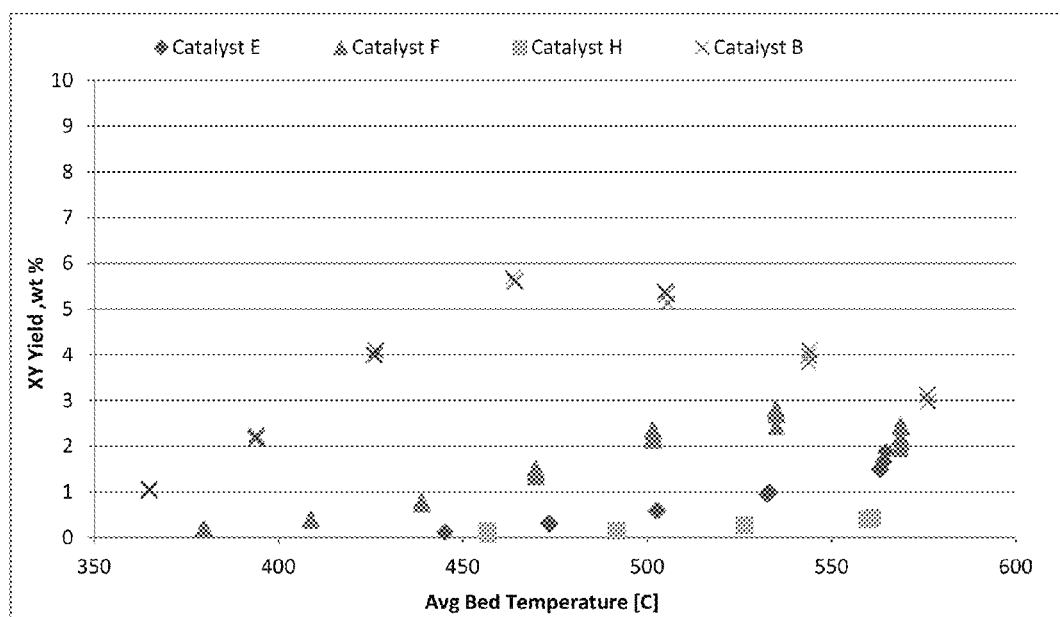
FIG. 22 is a graph showing a comparison of xylene yield as a function of bed temperature between rhenium and non-rhenium containing UZM-8 and MFI zeolite catalysts in accordance with the Examples provided herein.
Figure 23:
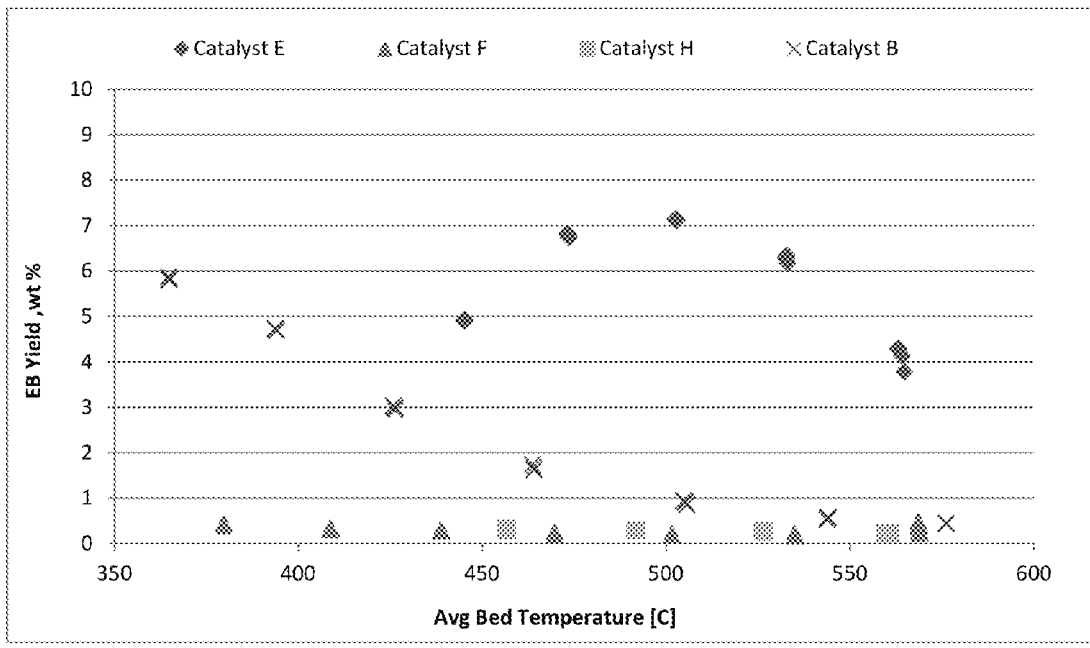
FIG. 23 is a graph showing a comparison of ethylbenzene yield as a function of bed temperature between rhenium and non-rhenium containing UZM-8 and MFI zeolite catalysts in accordance with the Examples provided herein.
Figure 24:
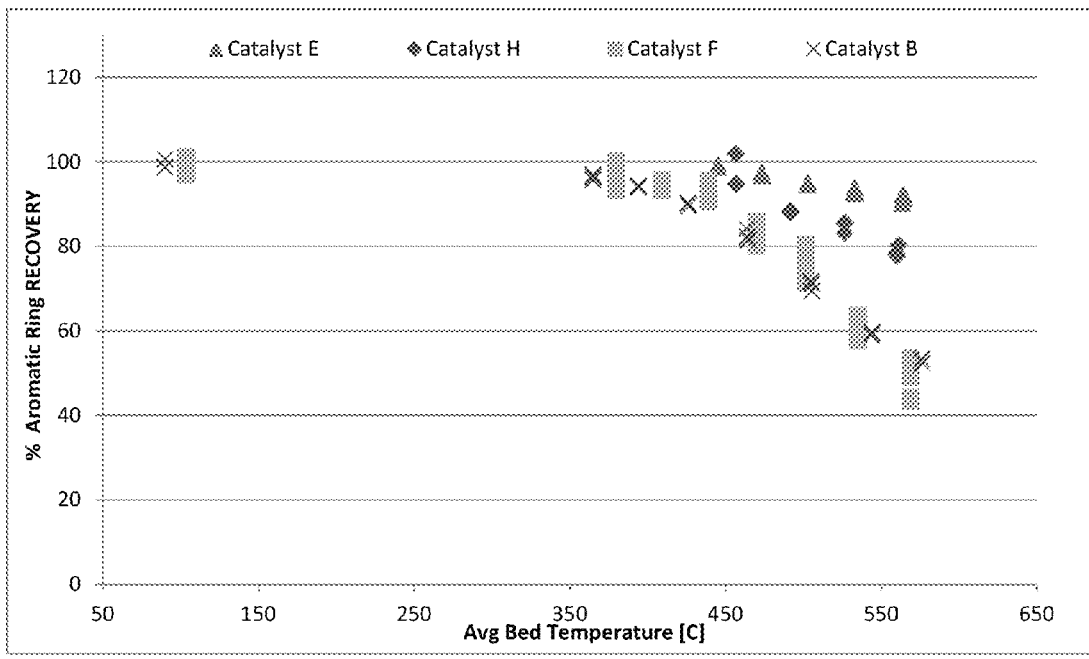
FIG. 24 is a graph showing a comparison of aromatic ring recovery as a function of bed temperature between rhenium and non-rhenium containing UZM-8 and MFI zeolite catalysts in accordance with the Examples provided herein.
Figure 25:
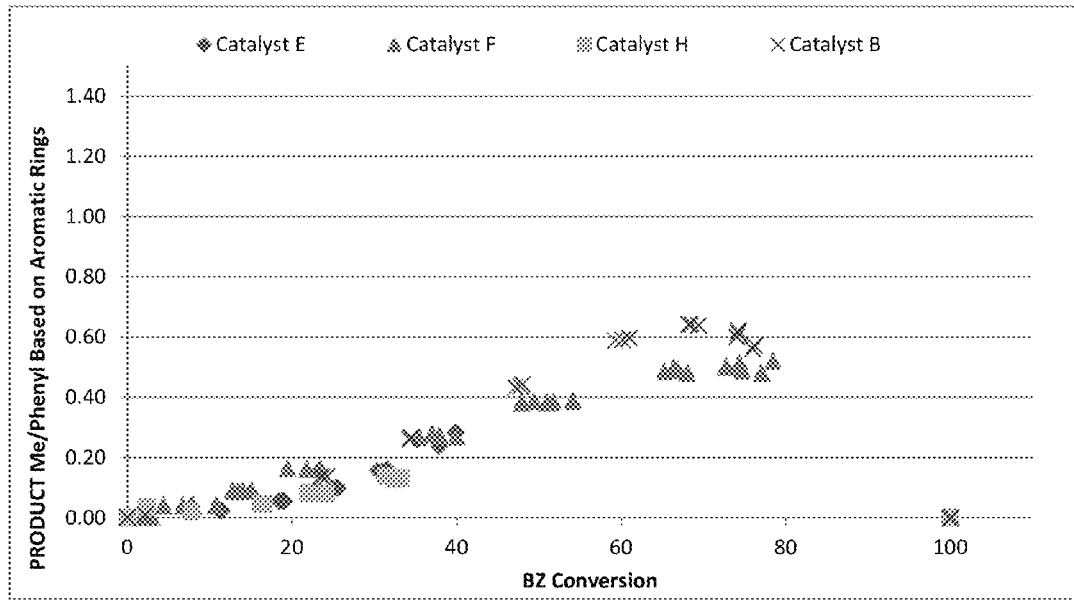
FIG. 25 is a graph showing a comparison of methyl to phenyl ratio as a function of benzene conversion between rhenium and non-rhenium containing UZM-8 and MFI zeolite catalysts in accordance with the Examples provided herein.

FIGS. 21-25 also provide a comparison between metal and non-metal containing catalysts to illustrate the effect that including a hydrogenation/dehydrogenation metal has on the catalyst activity and selectivity. FIGS. 21-25 compare the test results of Catalysts B, E, F, and H. As shown above, MFI with rhenium has poorer selectivity than MFI without rhenium to toluene, xylenes, and ethylbenzene. FIGS. 21-23 further illustrate that the UZM-8 zeolite catalyst that shows poorer selectivity than the MFI zeolite catalysts has even worse selectivity when it includes rhenium.

Example 8

The catalysts as provided in Table 3 below were prepared and tested as described below.

TABLE 3

Compositions of the tested catalyst samples.

| Catalyst | Zeolite | Metal | Binder |
|---|---|---|---|
| K | 75 wt % MFI | None | $Al_2O_3$ |
| L | 65 wt % MFI | None | ALPO |
| M | 65 wt % MFI | None | $SiO_2$ |
| N | 70 wt % MFI | None | $ZrO_2$ |
| O | 75 wt % MFI | None | $Al_2O_3$ |

Catalyst K was prepared by the same method as Catalysts B and J described above and included MFI zeolite with a Si/Al2 ratio of 23.

Catalyst L included MFI zeolite with a Si/Al2 ratio of 40. Catalyst L was prepared by oil dropping a slurry of MFI in an amorphous aluminum phosphate matrix and neutralizing/gelling with hexamethylenetetraamine (HMT). The oil-dropped spheres were then pressure-aged, washed until free of Cl, dried and finally calcined in air at 650° C. for 4 hours to produce a spherical support.

Catalyst M was prepared to include an MFI zeolite with a Si/Al2 ratio of 40. Catalyst M was prepared by forming of the Zeolite with suitable sources of colloidal silica such as Ludox™ and precipitated silica such as Hi-Sil™, and extrusion aid such as Methocel™. In the binder the mass ratio of Ludox™ to Hi-Sil™ was kept at 20% to 15%. To the extrusion mixture 1.5% Methocel™ was also added. The catalysts were extruded into 1/16" cylinder shapes. Before testing the formed dried extrudates were calcined at 550° C. for two hours and ion exchanged at least three times for the appropriate proton form of the catalyst before any testing.

Catalyst N included MFI zeolite with a Si/Al2 ratio of 40. Catalyst N was prepared by oil dropping a slurry of MFI in a zirconyl hydroxynitrate matrix and neutralizing/gelling with HMT. The oil-dropped spheres are then aged, washed (until nitrate-free), dried and finally calcined at a temperature of at least 550° C. for 2 hours. Before testing the formed particles were calcined and ion exchanged at least three times as necessary for the appropriate proton form of the catalyst before any testing.

For testing each of the catalysts K-N, 1 gram of 40-60 mesh sample of the catalyst was loaded in a quartz lined fixed bed reactor. At 400 psig with hydrogen flow the catalyst bed was heated to 550° C. (at a rate of 5° C./min), followed by a 2 hour hold at 550° C. Hydrogen flow was set to be the same rate imposed during the hydrocarbon test phase. The hydrocarbon testing phase was resumed in four different temperatures to change conversion. The maximum temperature at 550° C. was the first temperature condition.

The total reactor effluent for each test was analyzed with an on-line GC employing a boiling point column. To make the on-line analysis practical, all species peaks eluting after ortho-Xylene were categorized as C9+ heavies. The meta-Xylene and para-Xylene are also reported in sum within this on-line GC method set-up. The total reactor effluent gas composition was obtained using a single on-line GC system, employing a single DB-1 boiling point column. The GC measured total reactor effluent gas composition approximately every 22 minutes, which equates to 5 GC analyses at each of the four hold temperatures of the reactor temperature profile. Specifications of the GC analysis method used included:

Oven: Hold at 40° C., 2.5 minutes, Ramp 12° C./min to 200° C., hold 1.37 minutes.
Columns: 30 m×0.320 μm×1.0 μm J&W 123-1033 DB-1 type column
Carrier gas: H2 @ 41 cm/sec avg. linear velocity
Split Ratio: 400:1
Gas Sampling: 250 uL Valco gas sampling valve
Total Gas effluent analysis with FID detector. Sum of all HCBN's=100%.

The hydrocarbon (HC) feed was nominally 50% by weight Benzene and the balance n-pentane. Test conditions were set at 400 psig, at a hydrogen-to-hydrocarbon ratio of 4 $H_2$:HC, and 2.5 WHSV. As specified for some tests a hydrocarbon feed with nominally 50% Ethane and 50% Benzene by weight was also employed at test conditions 400 psig, 0 or 0.2 $H_2$:HC, 2.5 or 1 WHSV.

Catalyst O was prepared and tested with a hydrocarbon feed containing ethane and Benzene. Catalyst O was made in the same manner as Catalysts K, J, and B described above.

Catalyst O was tested using a different protocol. Catalyst O was tested using a feed that had nominally 50-50 by weight Benzene and Ethane as presented in Table 4 below. The test conditions included a pressure of 400 psig, a 0 or 0.2 hydrogen to hydrocarbon ratio, and 1 WHSV. The A10+ reported component includes C10+ aromatics (including Naphthalenes) and unknown components.

Figure 26:
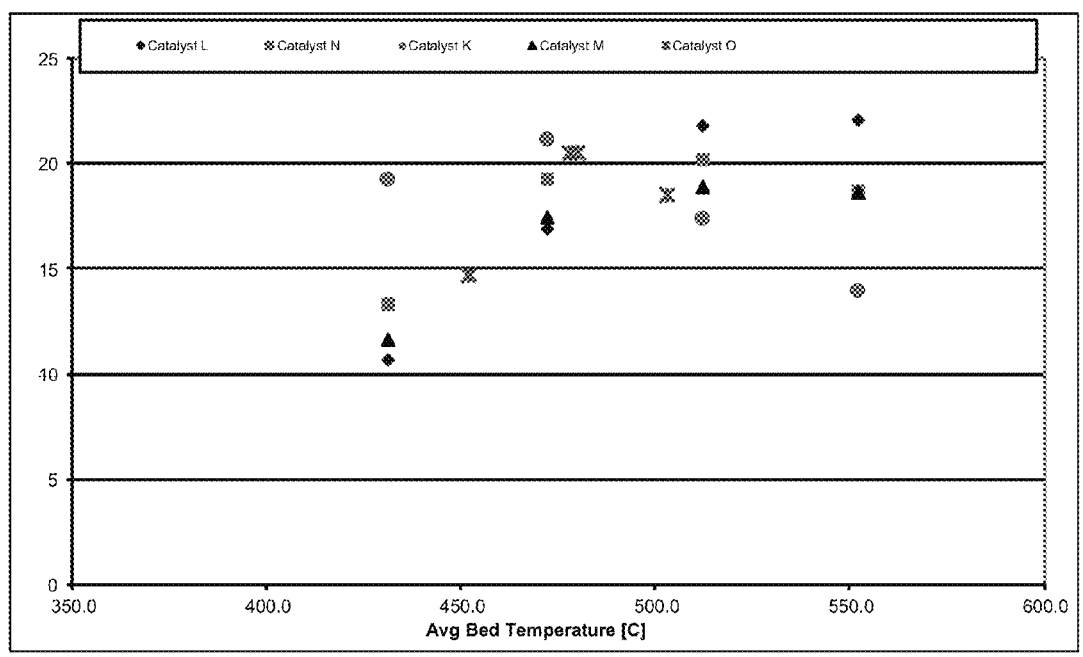
FIG. 26 is a graph showing a comparison of toluene yield as a function of bed temperature between Catalysts K, L, M, N, O in accordance with the Examples provided herein.
Figure 27:
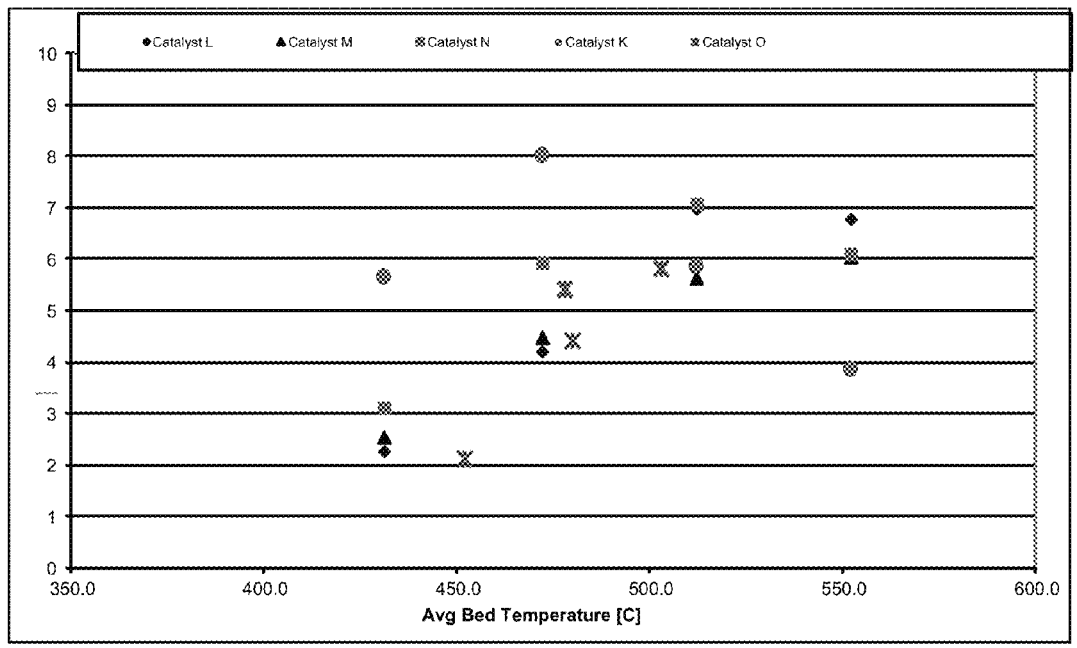
FIG. 27 is a graph showing a % Xylene Yield at the conditions of FIG. 26 in accordance with the Examples provided herein.

FIGS. 26 and 27 depict the weight % of Toluene and Xylene in the total hydrocarbon reactor effluent. FIGS. 26 and 27 illustrate that all Catalysts, K, L, M, N, and O perform equivalently in terms of major methylated aromatic ring production despite using different binders and different paraffinic feedstocks.

Example 9

The catalysts provided in Table 4 below were prepared and tested as described below.

TABLE 5

Compositions of the tested catalyst samples.

| Catalyst | Zeolite | Metal | Binder |
|---|---|---|---|
| P | 75 wt % MFI | 0.1 wt % Ni | $Al_2O_3$ |
| Q | 75 wt % MFI | 0.3 wt % Ni | $Al_2O_3$ |
| R | 75 wt % MFI | 1.0 wt % Ni | $Al_2O_3$ |

Catalysts P, Q, and R were prepared by impregnating nickel on Catalyst K described previously. The Nickel impregnation procedure used is the same as described previously for Catalyst A. Catalysts P, Q, R K, and F were tested by the same method described above for Catalysts K-N.

Figure 28:
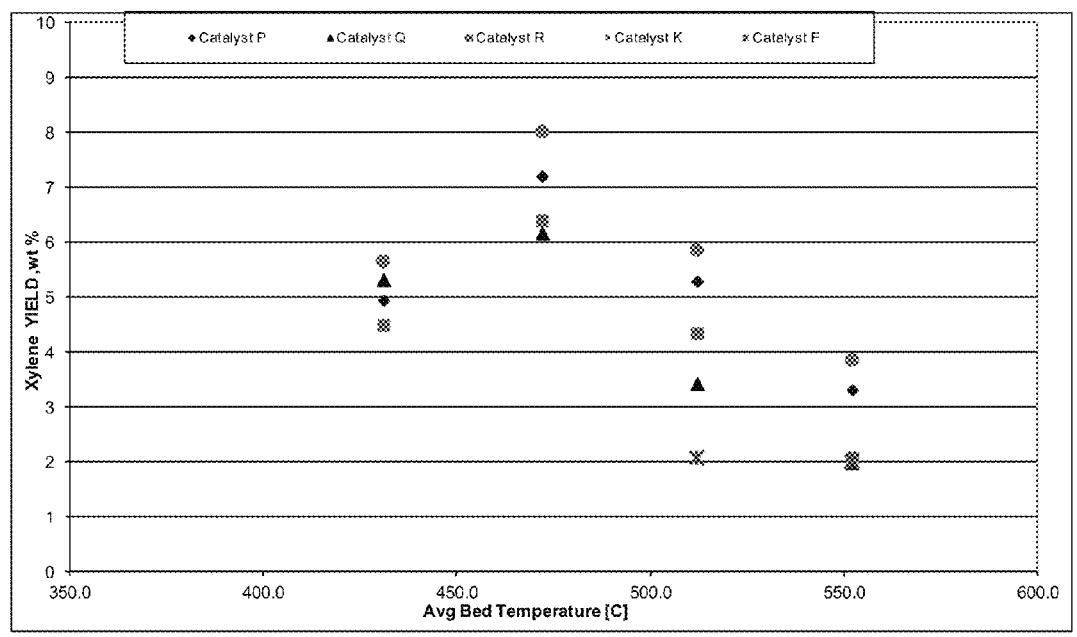
FIG. 28 is a graph showing a comparison of Xylene yield as a function of bed temperature between Catalysts F, K, P, Q, R in accordance with the Examples provided herein.
Figure 29:
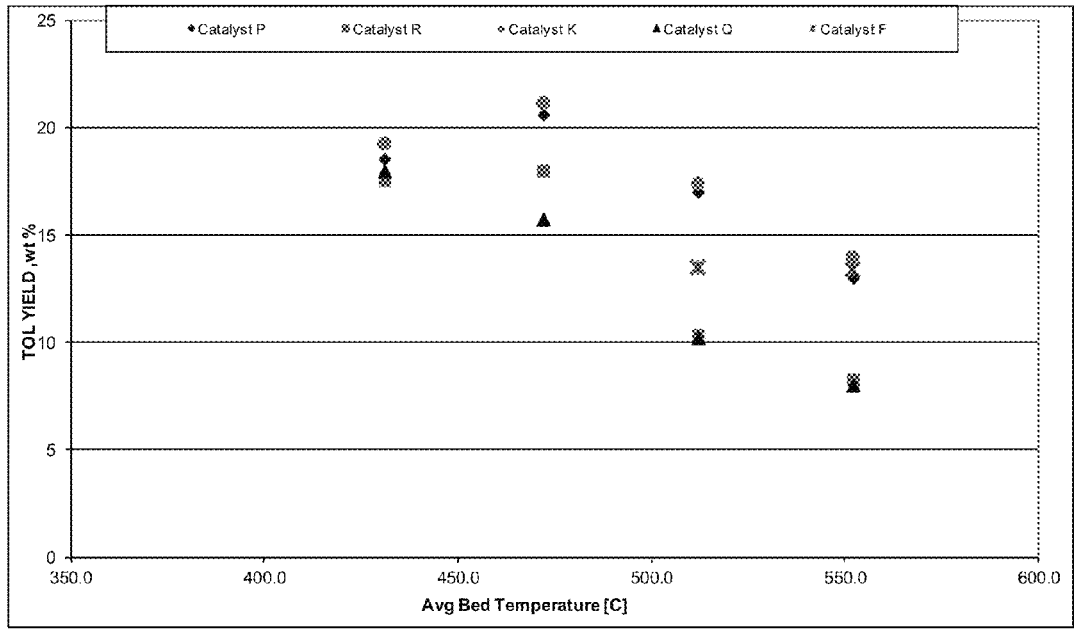
FIG. 29 is a graph showing a comparison of Toluene yield as a function of bed temperature between Catalysts F, K, P, Q, R in accordance with the Examples provided herein.

FIG. 28 depicts the % Xylene yield as a function of catalyst bed temperature. Catalyst K with no Nickel has the highest Xylene yield among all metal modified catalysts, Catalysts P, Q, R and F. Among the Nickel modified catalysts, Catalyst P with the lowest Nickel content at 0.1 wt % is the closest to the performance of K. FIG. 29 depicts the Toluene yield. Again Catalyst K with no Nickel provided the highest Toluene yield and Catalyst P with the lowest Nickel content at 0.1 wt % is the closest in performance to Catalyst K.

TABLE 4

Catalyst O Ethane-Benzene Test Results.

|  | Run A | Run B | Run C | Run D | Run F | Run G | Run H | Run I |
|---|---|---|---|---|---|---|---|---|
| Temp | 476 | 341 | 452 | 478 | 503 | 476 | 480 | 477 |
| $H_2$:HCBN | 0 | 0 | 0 | 0 | 0 | 0 | 0.18 | 0 |
| FEED (wt. %) | | | | | | | | |
| Ethane | 0 | 43.4 | 43.4 | 43.4 | 43.4 | 43.4 | 43.4 | 43.4 |
| BZ | 100 | 56.6 | 56.6 | 56.6 | 56.6 | 56.6 | 56.6 | 56.6 |
| PRODUCT (wt. %) | | | | | | | | |
| Methane | 0.00 | 0.00 | 0.7 | 1.9 | 4.3 | 0.3 | 1.8 | 0.5 |
| Ethane | 0.00 | 43 | 36.5 | 35.2 | 34.2 | 31.1 | 33.6 | 37.8 |
| Ethylene | 0.00 | 0.00 | 0.2 | 0.5 | 0.7 | 0.1 | 0.3 | 0.1 |
| C3-C6 Paraffins | 0.00 | 0.00 | 0.00 | 0.00 | 0.00 | 0.00 | 0.00 | 0.00 |
| BZ | 99.4 | 55 | 39.6 | 25.4 | 19.3 | 55.3 | 31.9 | 45.5 |
| Tol. | 0.1 | 0.3 | 14.7 | 20.5 | 18.5 | 8.9 | 20.5 | 11.2 |
| EB + Styrene | 0.1 | 0.9 | 0.9 | 1.0 | 0.8 | 1.0 | 1.3 | 1.0 |
| XY | 0.0 | 0.1 | 2.1 | 5.4 | 5.8 | 0.8 | 4.4 | 1.2 |
| A9 Aromatics | 0.0 | 0.0 | 0.4 | 0.9 | 1.1 | 1.9 | 5.0 | 0.2 |
| A10+ Aromatics | 0.4 | 0.7 | 4.9 | 9.2 | 15.3 | 0.6 | 1.2 | 2.5 |
| TOTAL | 100.00 | 100.0 | 100.0 | 100.0 | 100.0 | 100.0 | 100.0 | 100.0 |
| Ethane % Conversion | 0.6 | 0.9 | 15.9 | 18.9 | 21.2 | 28.3 | 22.6 | 12.9 |
| BZ % Conversion | 0.0 | 2.8 | 30.0 | 55.1 | 65.9 | 2.3 | 43.6 | 19.6 |
| Phenyl Ring Retention mol % | 0.0 | 99 | 104 | 99 | 95 | 117 | 104 | 104 |
| Methyl/Phenyl Mole Ratio | 0.00 | 0.00 | 0.3 | 0.5 | 0.5 | 0.2 | 0.5 | 0.2 |

Example 10

The catalysts provided in Table 6 below were prepared and tested as described below.

TABLE 6

Compositions of the tested catalyst samples.

| Catalyst | Zeolite | Metal | Binder |
|---|---|---|---|
| S | 65 wt % MFI | 0.3 wt % Ni | $SiO_2$ |
| T | 70 wt % MFI | 0.3 wt % Ni | $ZrO_2$ |

Catalyst S was prepared by impregnating Nickel on Catalyst M. The Nickel impregnation procedure used is the same as described previously for Catalyst A. Catalyst T was prepared by impregnating Nickel on Catalyst N. The Nickel impregnation procedure used is the same as described previously for Catalyst A. Catalysts S, T, M, and N were tested for performance by the same method described above for Catalysts K-N.

Figure 30:
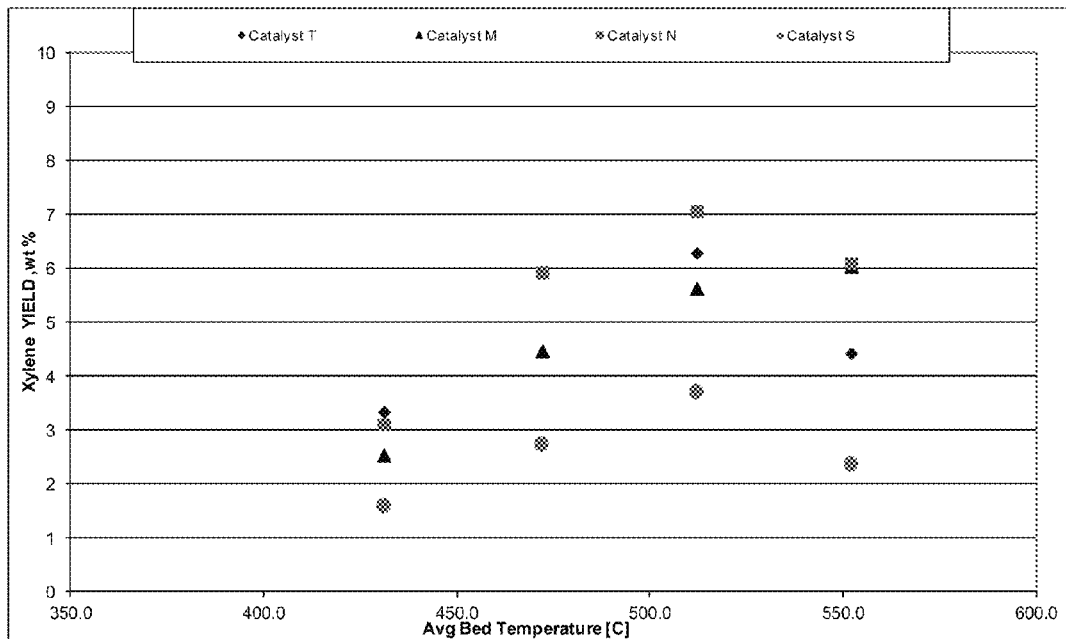
FIG. 30 is a graph showing a comparison of Xylene yield as a function of bed temperature between Catalysts S and M plus Catalysts T and N in accordance with the Examples provided herein.
Figure 31:
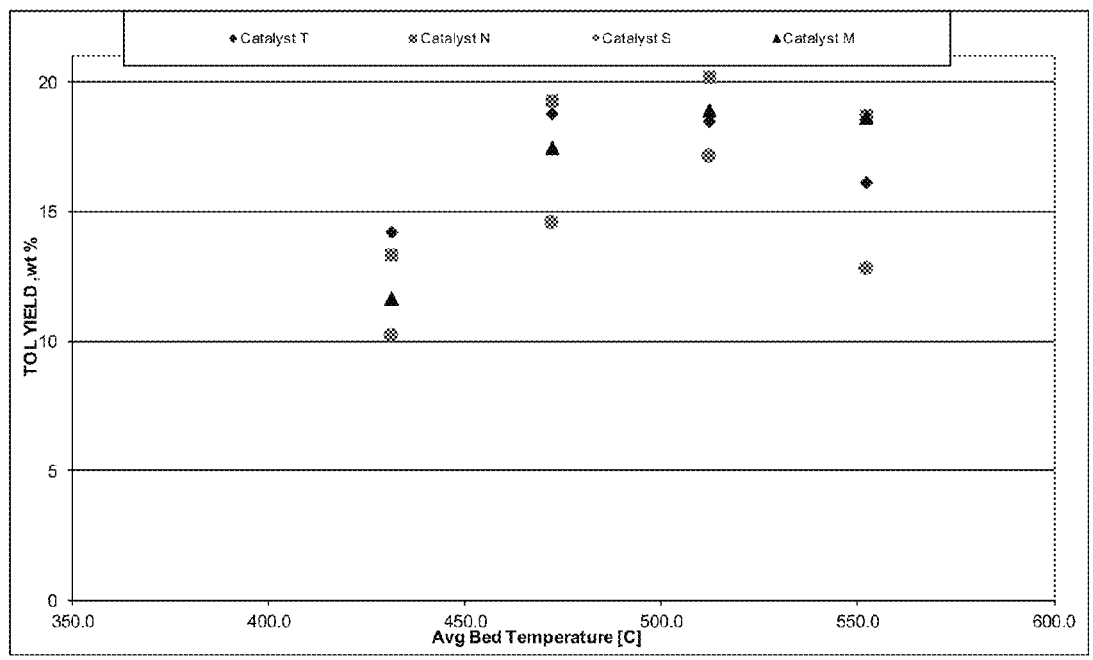
FIG. 31 is a graph showing a comparison of Toluene yield as a function of bed temperature between Catalysts S and M plus Catalysts T and N in accordance with the Examples provided herein.

FIGS. 30 and 31 depict the Xylene and Toluene yields respectively. Comparing Catalyst T and N for the Nickel containing Catalyst T both the Xylene and Toluene yields are lower than the no-metals counterpart, Catalyst N. Comparing Catalyst S and M for the Nickel containing Catalyst S both the Xylene and Toluene yields are also lower than the no-metals counterpart, Catalyst M.

Example 11

The catalysts provided in Table 7 below were prepared and tested as described below.

TABLE 7

Compositions of the tested catalyst samples.

| Catalyst | Zeolite | Metal | Binder |
|---|---|---|---|
| U | 75 wt % MTW | None | $SiO_2$ |
| V | 75 wt % MTW | 0.3 wt % Ni | $SiO_2$ |
| W | 75 wt % MOR | None | $SiO_2$ |
| X | 75 wt % MOR | 0.3 wt % Ni | $SiO_2$ |

Catalyst U was prepared using a procedure similar to what was described for Catalyst M. For Catalyst U the proper amount of MTW zeolite per Table 7 was formed with Silica and other forming agents as described for Catalyst M.

Catalyst V was prepared by impregnating Nickel on Catalyst U. The Nickel impregnation procedure used is the same as described previously for Catalyst A.

Catalyst W was prepared using a procedure similar to what was described for Catalyst M and U. For Catalyst W the proper amount of MOR zeolite per Table 7 was formed with Silica and other forming agents as described for Catalyst M.

Catalyst X was prepared by impregnating Nickel on Catalyst W. The Nickel impregnation procedure used is the same as described previously for Catalyst A.

Figure 32:
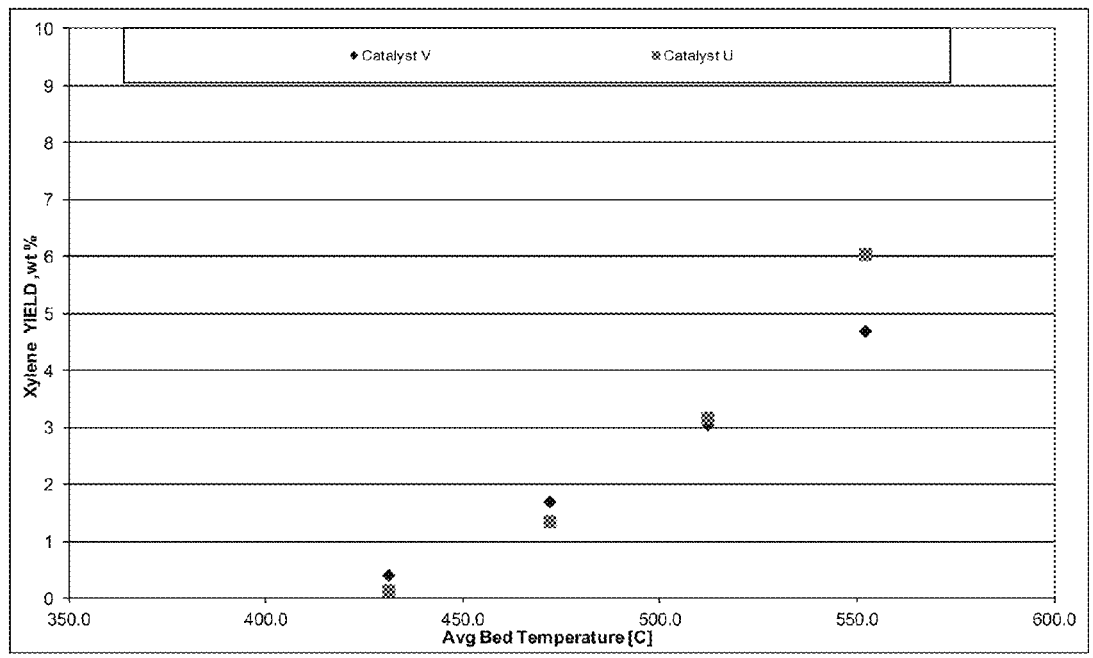
FIG. 32 is a graph showing a comparison of Xylene yield as a function of bed temperature between Catalysts U and V in accordance with the Examples provided herein.
Figure 33:
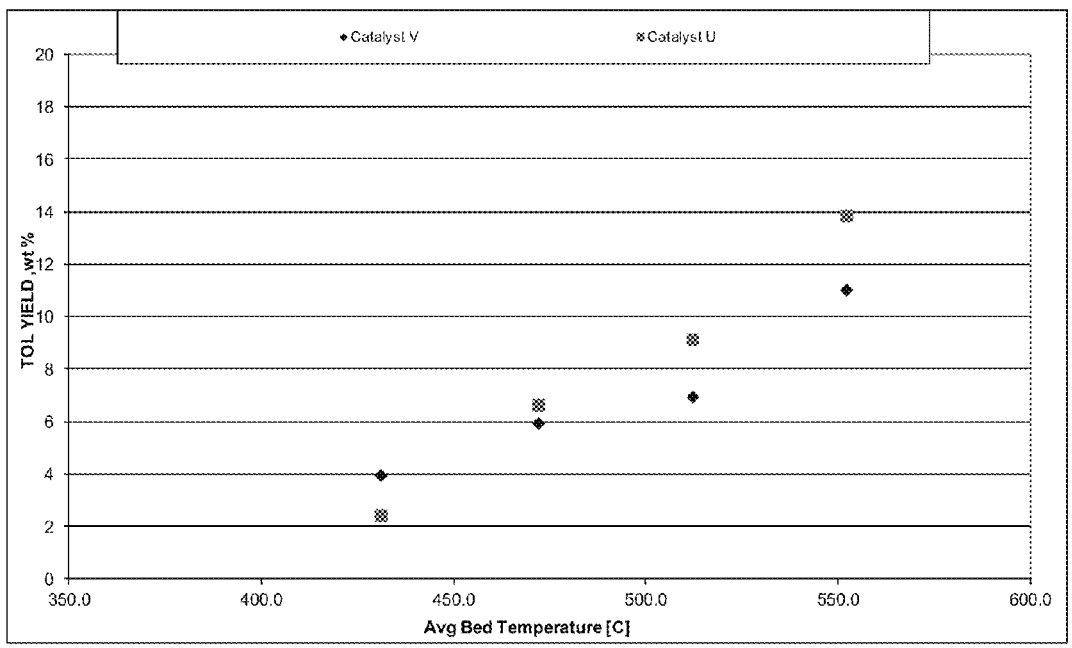
FIG. 33 is a graph showing a comparison of Toluene yield as a function of bed temperature between Catalysts U and V in accordance with the Examples provided herein.

FIGS. 32 and 33 depict the Xylene and Toluene yields, respectively for Catalysts U and V. The Nickel containing Catalyst V has a lower yield of Xylene and Toluene than the metal free counterpart.

Figure 34:
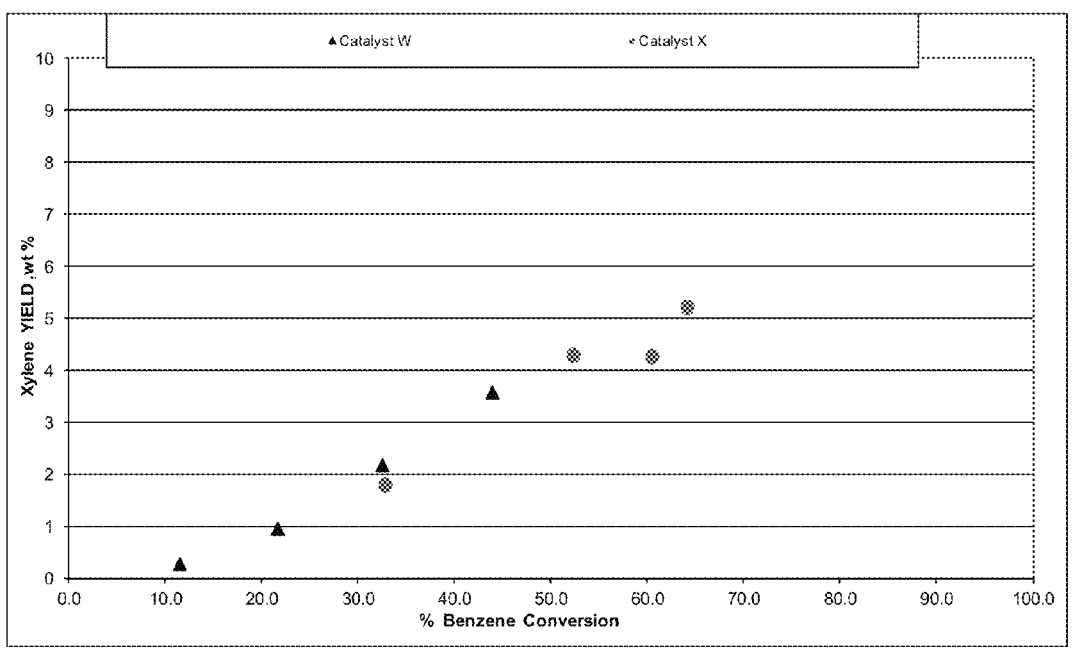
FIG. 34 is a graph showing a comparison of Xylene yield versus Benzene Conversion between Catalysts W and X in accordance with the Examples provided herein.
Figure 35:
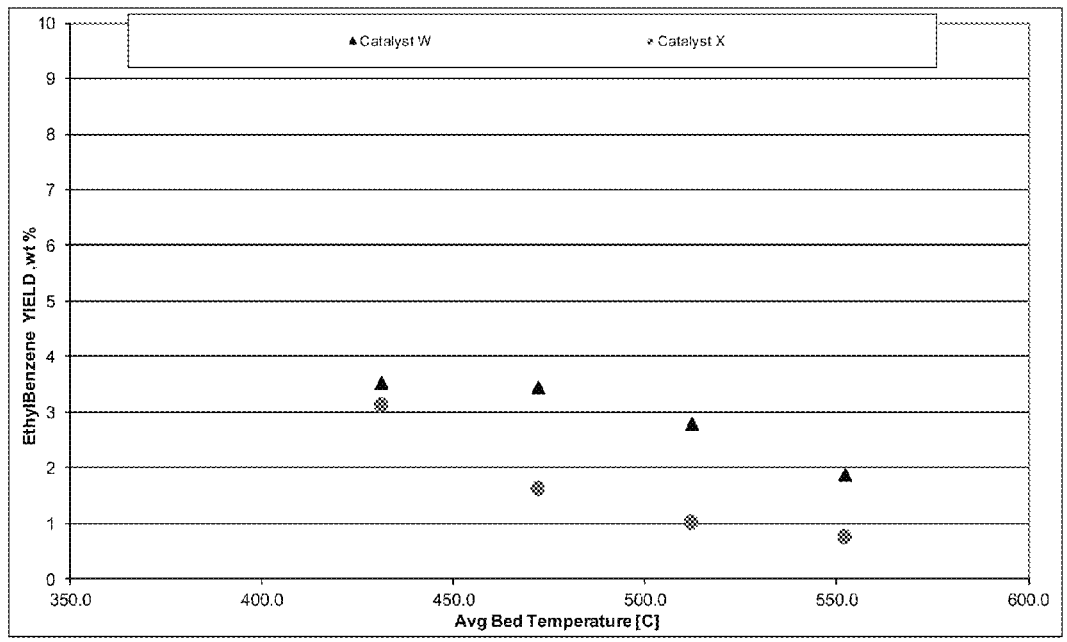
FIG. 35 is a graph showing a comparison of EthylBenzene yield as a function of bed temperature between Catalysts W and X in accordance with the Examples provided herein.
Figure 36:
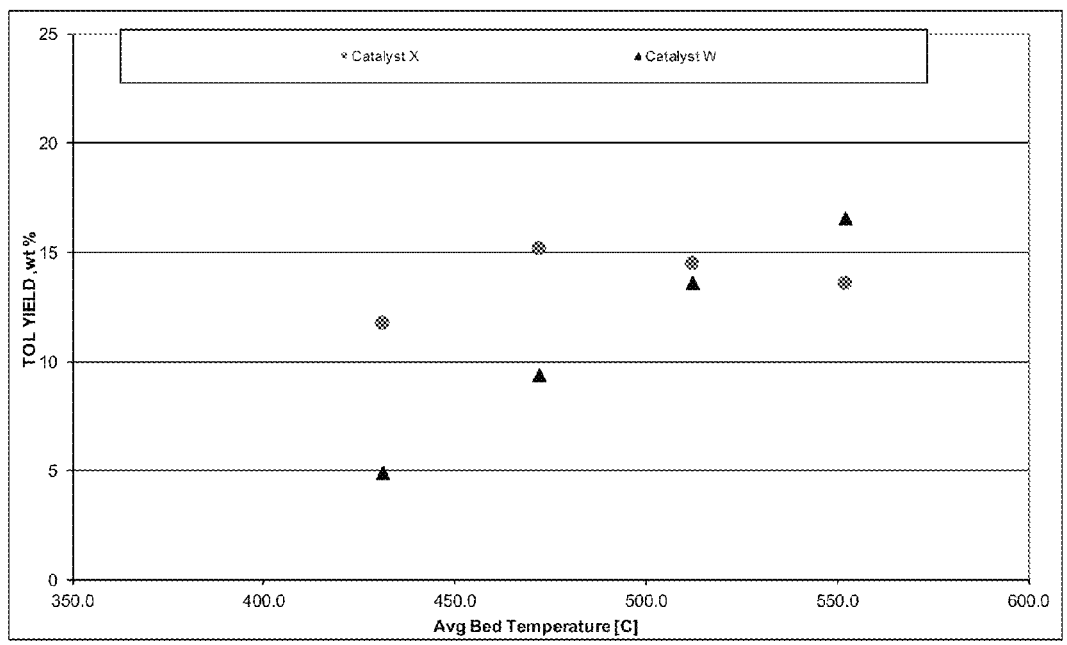
FIG. 36 is a graph showing a comparison of Toluene yield as a function of bed temperature between Catalysts W and X in accordance with the Examples provided herein.
Figure 37:
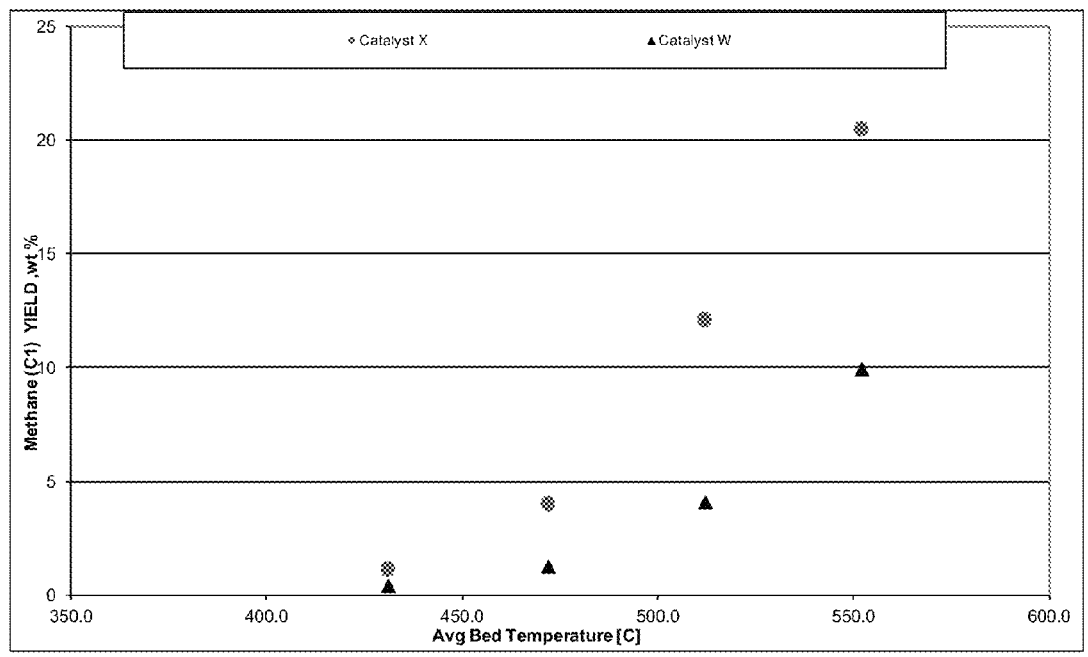
FIG. 37 is a graph showing a comparison of Methane yield as a function of bed temperature between Catalysts W and X in accordance with the Examples provided herein.

FIGS. 34 and 35 depict performance results for Catalysts W and X. FIG. 34 depicts the Xylene yield versus Benzene conversion for the two catalysts. The Nickel containing Catalyst X, at the same Benzene conversion shows a lower Xylene Yield compared to Catalyst W. FIG. 35 depicts the ethylbenzene yield versus bed temperature. The Nickel containing Catalyst X has lower ethylbenzene yield compared to the non-metal containing Catalyst W. FIG. 36 depicts the Toluene yield for Catalysts X and W. The non-metal containing Catalyst W achieves a higher Toluene yield towards elevated temperatures compared to the low Toluene yield of the metal containing Catalyst X. FIG. 37 depicts the Methane yield for both catalysts. The Nickel containing Catalyst X has much higher methane yield than the non-metal Catalyst W.

Example 12

The catalyst provided in Table 8 below was prepared.

TABLE 8

Compositions of the tested catalyst samples.

| Catalyst | Zeolite | Metal | Binder |
|---|---|---|---|
| Y | 75 wt % MFI | None | $Al_2O_3$ |

Catalyst Y was prepared by the same method as Catalysts K, B and J described above and included MFI zeolite with a Si/Al2 ratio of 23.

A new set of tests were conducted using Catalysts Y, Q, and A with a hydrocarbon feed containing ethane and Benzene. The testing procedures were the same as described earlier for the normal-pentane and Benzene feed tests. The feedstock was nominally 50% by weight Benzene and the balance Ethane. Test conditions were set at 400 psig, 0.5 $H_2$:HC, 1.0 WHSV.

Figure 38:
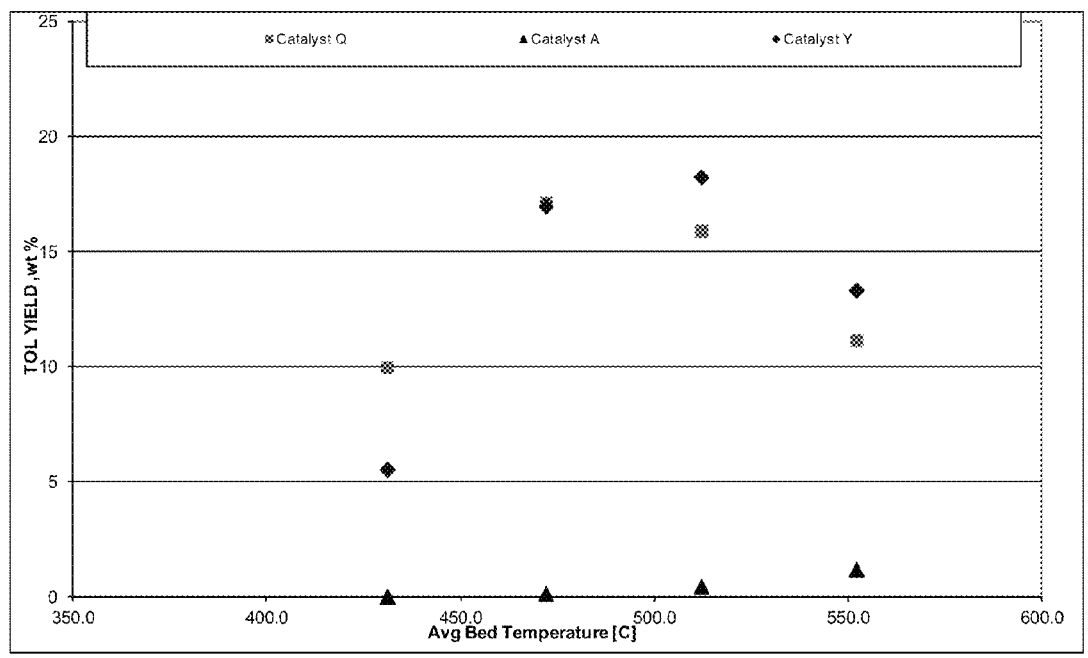
FIG. 38 is a graph showing a comparison of Toluene yield as a function of bed temperature between Catalysts Y, Q and A in accordance with the Examples provided herein.
Figure 39:
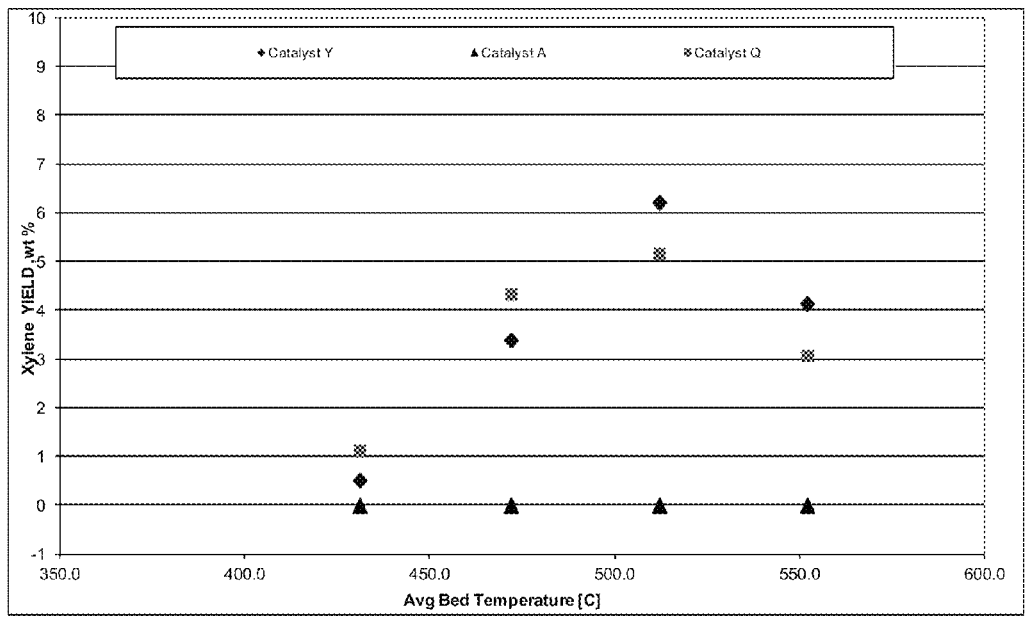
FIG. 39 is a graph showing a comparison of Xylene yield as a function of bed temperature between Catalysts Y, Q and A in accordance with the Examples provided herein.

FIG. 38 depicts the Toluene yield versus bed temperature for Catalysts Y, Q, and A. The Catalyst A without any zeolite in it has no Toluene yield. Catalyst Q with 0.3 wt % Nickel metal has lower Toluene yield than Catalyst Y without any metals. FIG. 39 depicts the Xylene yield versus bed temperature for Catalysts Y, Q, and A. Catalyst A with zero % Xylene in the product, shows no Xylene yield. Catalyst Q comprising 0.3 wt % Nickel has lower Xylene yield than Catalyst Y.

Example 13

A new set of tests were conducted using Catalysts Y, L, M, U, and W with a hydrocarbon feed containing 50% ethane and 50% Benzene by weight as described above for Example 12.

Figure 40:
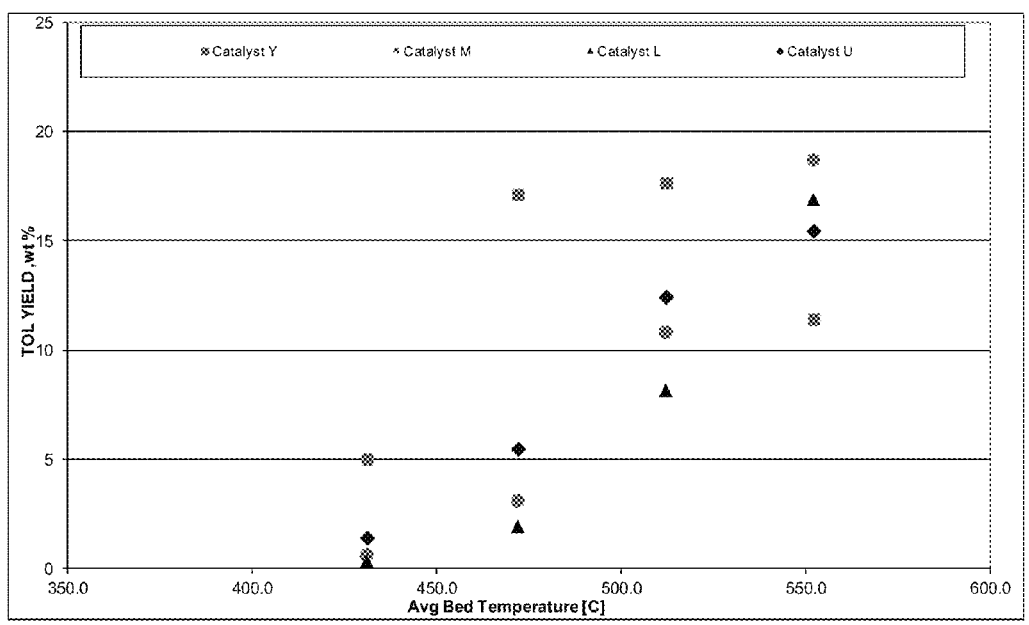
FIG. 40 is a graph showing a comparison of Toluene yield as a function of bed temperature between Catalysts L, M, U, and Y in accordance with the Examples provided herein.
Figure 41:
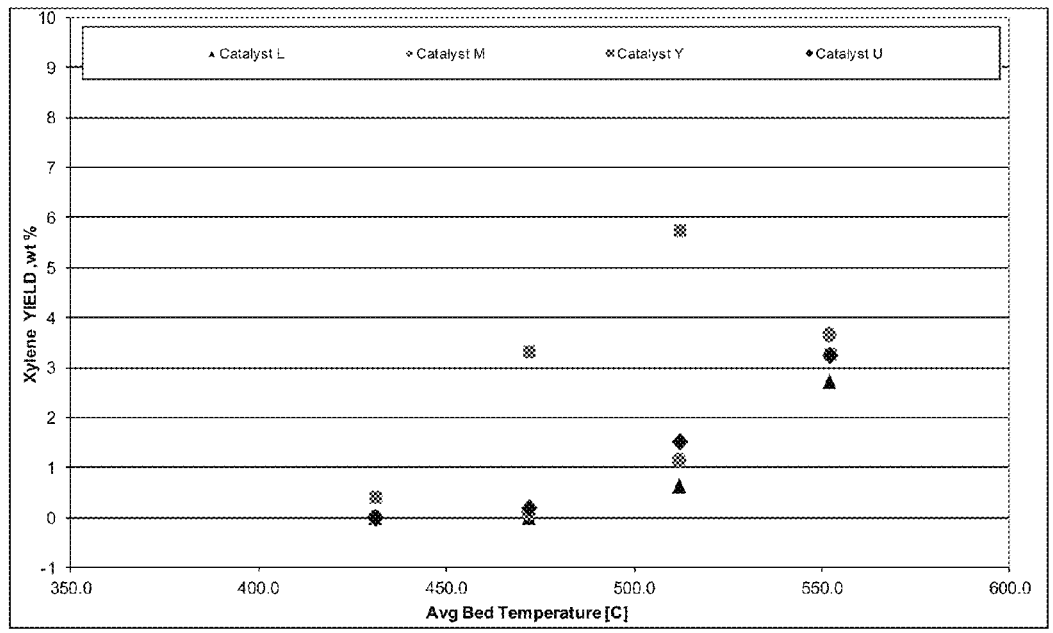
FIG. 41 is a graph showing a comparison of Xylene yield as a function of bed temperature between Catalysts L, M, U, and Y in accordance with the Examples provided herein.

FIGS. 40 and 41 depict the Toluene and Xylene yields as a function of reactor temperature. Catalyst W, results not shown in these figures, tested poorer than M and U, while the best performer was Catalyst Y. For showing the impact of a hydrogenation capable metal, such as Platinum, besides Catalyst Y, the researchers selected Catalysts M and U. Catalyst M was selected over Catalyst L due to its higher Toluene and Xylene yield.

Example 14

The catalysts provided in Table 9 below were prepared.

TABLE 9

Compositions of the tested catalyst samples.

| Catalyst | Zeolite | Metal | Binder |
|---|---|---|---|
| Z | 75 wt % MFI | 100 ppm Pt | $Al_2O_3$ |
| AA | 75 wt % MFI | 1000 ppm Pt | $Al_2O_3$ |

Catalysts Z and AA were prepared by impregnation of the required amount of Platinum on Catalyst Y according to the same procedure as described for Catalyst I.

Figure 42:
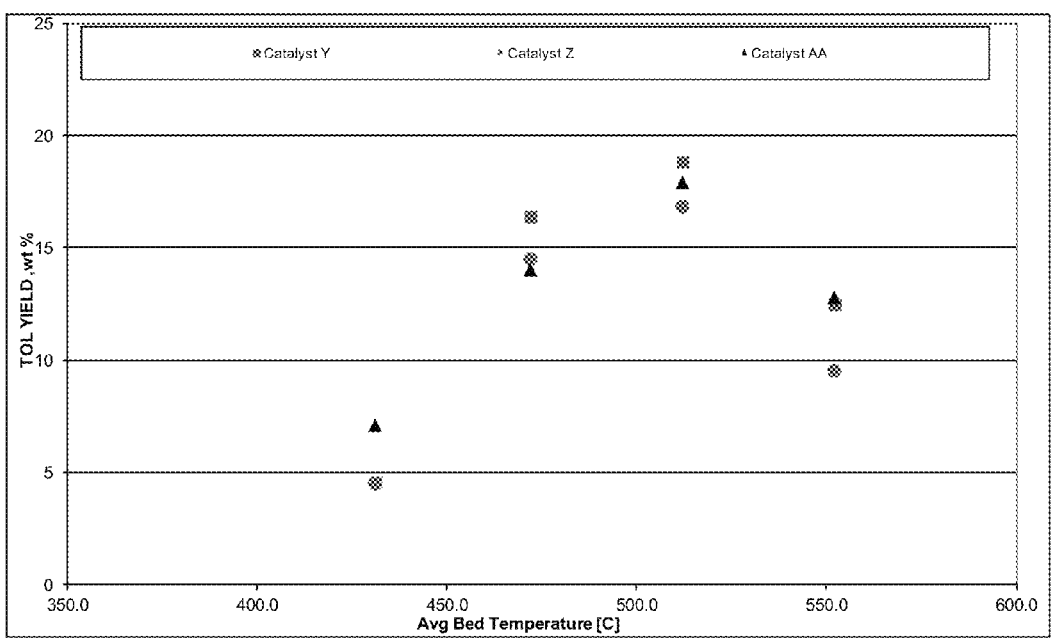
FIG. 42 is a graph showing a comparison of Toluene yield as a function of bed temperature between Catalysts Y, Z, and AA in accordance with the Examples provided herein.
Figure 43:
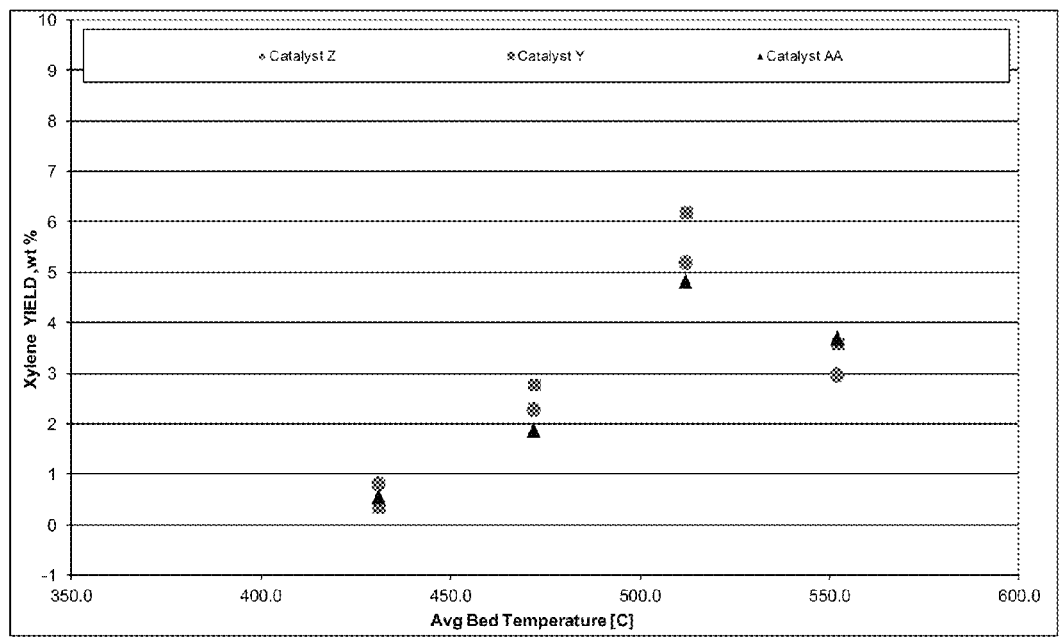
FIG. 43 is a graph showing a comparison of Xylene yield as a function of bed temperature between Catalysts Y, Z, and AA in accordance with the Examples provided herein.

FIGS. 42 and 43 depict the Toluene and Xylene yields as a function of reactor temperature. The test conditions were the same as described in Examples 12 and 13. The presence of Platinum even in small amounts for Catalysts Z and AA resulted in lower Toluene and Xylene yields compared to Catalyst Y. This observation was clear especially at temperatures where the maximum Xylene and Toluene yields are observed.

Example 15

The catalysts provided in Table 10 below were prepared.

TABLE 10

Compositions of the tested catalyst samples.

| Catalyst | Zeolite | Metal | Binder |
|---|---|---|---|
| AB | 75 wt % MTW | 100 ppm Pt | $SiO_2$ |
| AC | 75 wt % MTW | 1000 ppm Pt | $SiO_2$ |

Catalysts AB and AC were prepared by impregnation of the required amount of Platinum on Catalyst U according to the same procedure as described for Catalyst I.

Figure 44:
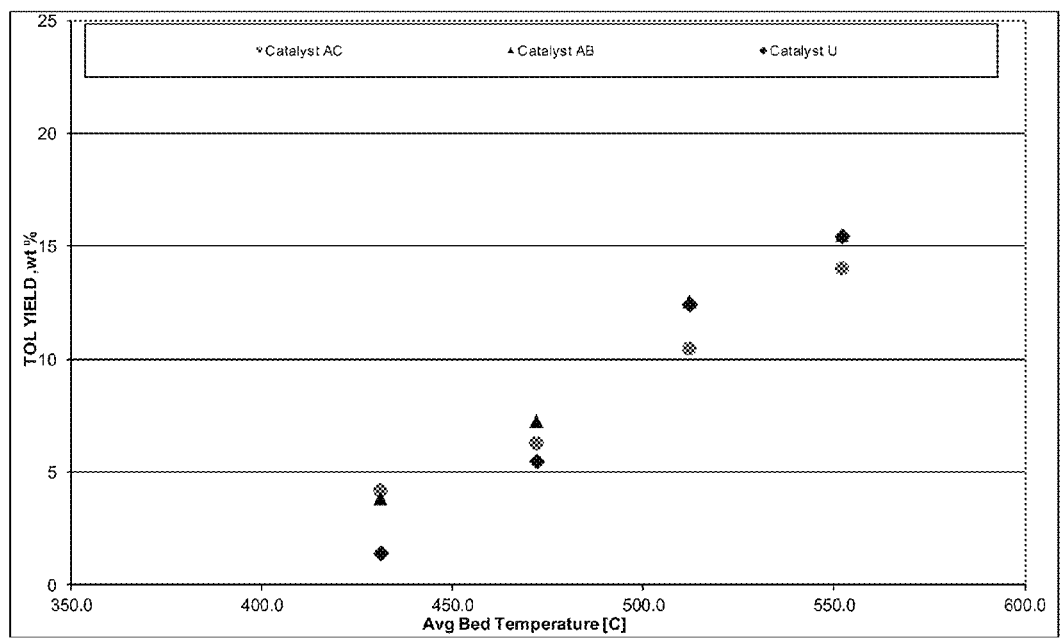
FIG. 44 is a graph showing a comparison of Toluene yield as a function of bed temperature between Catalysts U, AB, and AC in accordance with the Examples provided herein.
Figure 45:
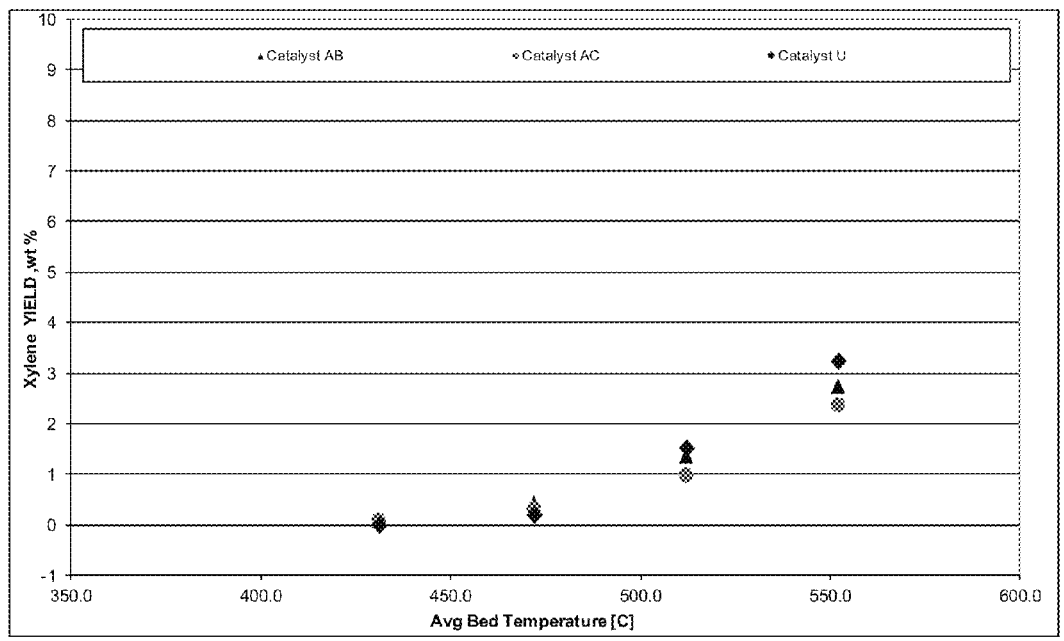
FIG. 45 is a graph showing a comparison of Xylene yield as a function of bed temperature between Catalysts U, AB, and AC in accordance with the Examples provided herein.

FIGS. 44 and 45 depict the Toluene and Xylene yields as a function of reactor temperature. The test conditions were the same as described in Examples 12, 13, and 14. Catalysts AB and AC with Platinum showed lower or at best equivalent yields with respect to Catalyst U. Consistent with Example 14, Example 15 also demonstrates the adverse impact on performance of having a hydrogenation function capable metal in the formulation. The adverse impact on performance increases with increased metal loading beyond a critical range. Example 15 illustrates the same adverse impact reported via Example 14. Example 15 catalysts contain an alternative zeolite MTW, and an alternative binder silica compared to the catalysts of Example 14.

Example 16

The catalysts provided in Table 11 below were prepared.

TABLE 11

Compositions of the tested catalyst samples.

| Catalyst | Zeolite | Metal | Binder |
|---|---|---|---|
| AD | 65 wt % MFI | 100 ppm Pt | $SiO_2$ |
| AE | 65 wt % MFI | 1000 ppm Pt | $SiO_2$ |

Figure 46:
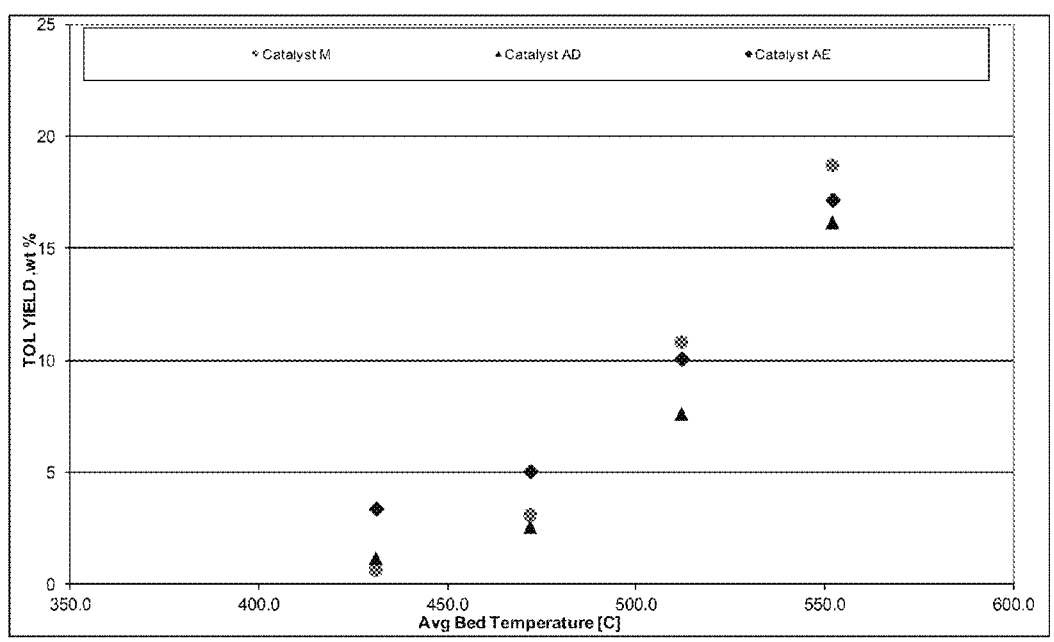
FIG. 46 is a graph showing a comparison of Toluene yield as a function of bed temperature between Catalysts M, AD, and AE in accordance with the Examples provided herein.
Figure 47:
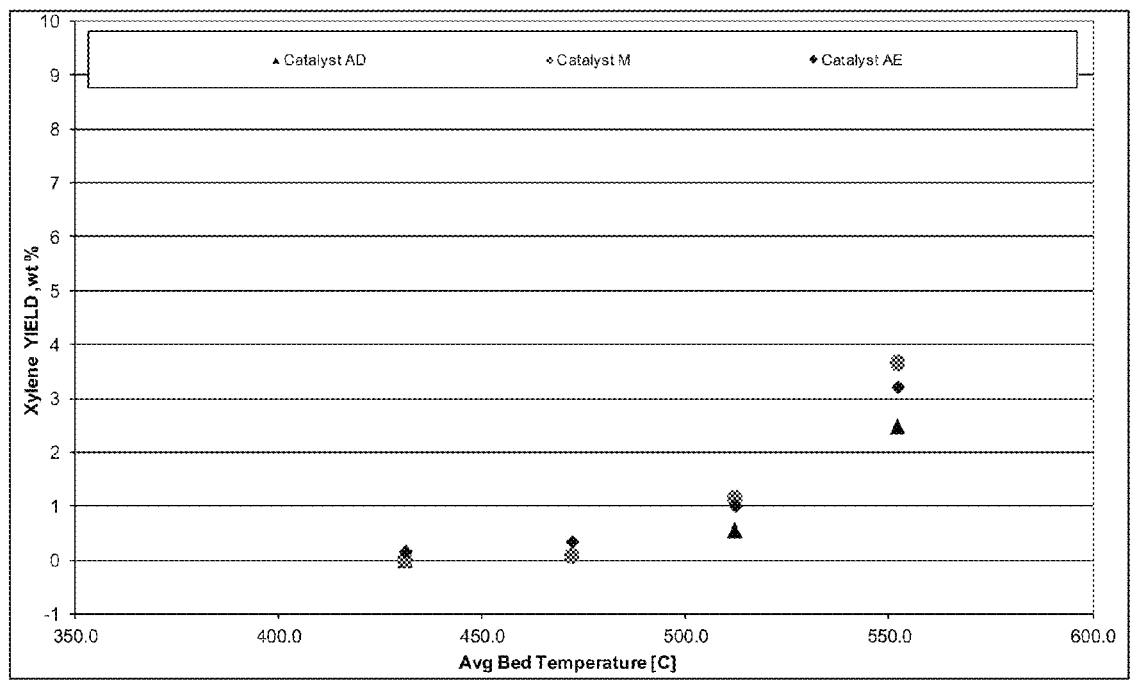
FIG. 47 is a graph showing a comparison of Xylene yield as a function of bed temperature between Catalysts M, AD, and AE in accordance with the Examples provided herein.

Catalysts AD and AE were prepared by impregnation of the required amount of Platinum on Catalyst M according to the same procedure as described for Catalyst I. FIGS. 46 and 47 depict the Toluene and Xylene yields as a function of reactor temperature. The test conditions were the same as described in Examples 12, 13, 14, and 15. Catalysts AD and AE with Platinum showed lower or at best equivalent yields with respect to Catalyst M. Consistent with prior examples, Example 16 also demonstrates the adverse impact on performance of having a hydrogenation function capable metal in the formulation. Example 16 catalysts contain yet another alternative zeolite MFI, and yet another alternative binder silica compared to the catalysts of Example 14.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for increasing a mole ratio of methyl to phenyl of one or more aromatic compounds in a feed, comprising:
   reacting an effective amount of one or more aromatic compounds and an effective amount of one or more aromatic methylating agents comprising at least one of an alkane, a cycloalkane, an alkane radical, and a cycloalkane radical in the presence of a catalyst consisting essentially of a MFI zeolite, an inorganic oxide binder, and an amount of Nickel metal of less than 0.1% by weight based on the weight of the catalyst at a temperature of less than 450° C. to form a product having a mole ratio of methyl to phenyl of at least about 0.1:1 greater than the feed.

2. The process according to claim 1, wherein the one or more aromatic methylating agents comprises compounds having at least two carbon atoms.

3. The process according to claim 1, wherein the one or more aromatic methylating agents comprises at least one of a cycloalkane and a C2-C8 alkane.

4. The process according to claim 1, wherein the one or more aromatic compounds comprises benzene.

5. The process according to claim 1, wherein the one or more aromatic compounds comprises toluene.

6. The process according to claim 1, wherein the catalyst comprises less than about 0.01% by weight based on the weight of the catalyst.

\* \* \* \* \*